(12) United States Patent
Kamohara et al.

(10) Patent No.: US 8,986,952 B2
(45) Date of Patent: Mar. 24, 2015

(54) ANTI-HUMAN NGF ANTIBODY

(75) Inventors: Masazumi Kamohara, Tokyo (JP); Hirotsugu Tanaka, Tokyo (JP); Yukari Koya, Tokyo (JP); Jun Takasaki, Tokyo (JP); Atsuo Yonezawa, Tokyo (JP); Eiji Yoshimi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/879,267

(22) PCT Filed: Aug. 10, 2012

(86) PCT No.: PCT/JP2012/070433
§ 371 (c)(1),
(2), (4) Date: Jul. 15, 2013

(87) PCT Pub. No.: WO2013/022083
PCT Pub. Date: Feb. 14, 2013

(65) Prior Publication Data
US 2014/0155582 A1  Jun. 5, 2014

(30) Foreign Application Priority Data

Aug. 11, 2011  (JP) ................................. 2011-176209
Dec. 8, 2011  (JP) ................................. 2011-269215

(51) Int. Cl.
| | | |
|---|---|---|
| C07K 16/22 | (2006.01) | |
| C12N 15/13 | (2006.01) | |
| C12N 15/63 | (2006.01) | |
| C12N 15/85 | (2006.01) | |
| A61K 47/48 | (2006.01) | |
| A61K 39/00 | (2006.01) | |

(52) U.S. Cl.
CPC ........... *C07K 16/22* (2013.01); *A61K 47/48215* (2013.01); *C07K 2317/76* (2013.01); *A61K 2039/505* (2013.01); *C07K 2317/21* (2013.01); *C07K 2317/24* (2013.01); *C07K 2317/33* (2013.01); *C07K 2317/55* (2013.01); *C07K 2317/94* (2013.01); *C12N 2510/02* (2013.01)
USPC .................. 435/69.1; 530/388.24; 435/320.1; 435/336

(58) Field of Classification Search
CPC ............... C07K 16/22; C07K 2317/51; C07K 2317/515; C07K 2317/21; C12N 15/63; C12N 15/85
See application file for complete search history.

(56) References Cited

U.S. PATENT DOCUMENTS

2009/0041717 A1  2/2009  MacDonald et al.
2011/0014208 A1  1/2011  MacDonald et al.

FOREIGN PATENT DOCUMENTS

| | | |
|---|---|---|
| JP | 2010 535509 | 11/2010 |
| WO | 02 096458 | 12/2002 |
| WO | 2004 058184 | 7/2004 |
| WO | 2005 019266 | 3/2005 |
| WO | 2005 061540 | 7/2005 |
| WO | 2006 077441 | 7/2006 |
| WO | 2006 110883 | 10/2006 |
| WO | 2010 128398 | 11/2010 |

OTHER PUBLICATIONS

Office Action issued Jul. 23, 2013 in Japanese Application No. 2013-525474 (With English Translation).
Garber, K., "Fate of novel painkiller mAbs hangs in balance," Nature Biotechnology, vol. 29, No. 3, Total 3 Pages, (Mar. 2011).
Indo, Y., et al., "Mutations in the TRKA/NGF receptor gene in patients with congenital insensitivity to pain with anhidrosis," nature genetics, vol. 13, pp. 485-488, (Aug. 1996).
Lane, N., et al., "Tanezumab for the Treatment of Pain from Osteoarthritis of the Knee," The New England Journal of Medicine, vol. 363, pp. 1521-1531, (Oct. 14, 2010).
"Dorsal Root Ganglion Neurons Are Destroyed by Exposure in utero to Maternal Antibody to Nerve Growth Factor," Science, vol. 210, pp. 916-918, (Nov. 21, 1980).
Evans, R., et al., "Proof of Concept Trial of Tanezumab for the Treatment of Symptoms Associated with Interstitial Cystitis," The Journal of Urology, vol. 185, pp. 1716-1721, (May 2011).
Katz, N., et al., "Efficacy and safety of tanezumab in the treatment of chronic low back paint," PAIN, vol. 152, pp. 2248-2258, (2011).
Sandroni, P., et al., "Congenital idiopathic inability to perceive pain: A new syndrome of insensitivity to pain and itch with preserved small fibers," PAIN, vol. 122, pp. 210-215, (2006).
Roopenian, D., et al., "FcRn: the neonatal Fc receptor comes of age," Nature Reviews Immunology, vol. 7, pp. 715-725, (Sep. 2007).
International Search Report Issued Sep. 11, 2012 in PCT/JP12/070433 Filed Aug. 10, 2012.
U.S. Appl. No. 13/762,908, filed Feb. 8, 2013, Kamohara, et al.

(Continued)

*Primary Examiner* — Robert C Hayes
(74) *Attorney, Agent, or Firm* — Oblon, McClelland, Maier & Neustadt, L.L.P.

(57) ABSTRACT

[Task] To provide an anti-human NGF antibody or an antigen-binding fragment thereof that is excellent in safety by reducing the risk of side effects such as effects on a fetus and thrombus formation while maintaining high neutralizing activity, and to provide means for preventing or treating various diseases in which human NGF is involved in the formation of pathological conditions, by using the antibody or the antibody-binding fragment thereof.

[Means for Resolution] An anti-human NGF antibody Fab' fragment comprising a heavy-chain variable region consisting of an amino acid sequence shown by SEQ ID NO:6 and a light-chain variable region consisting of an amino acid sequence shown by SEQ ID NO:4.

17 Claims, 1 Drawing Sheet

(56) References Cited

OTHER PUBLICATIONS

Office Action issued Oct. 28, 2014 in corresponding Chinese patent application No. 201280039293.3 with English translation, 21 pp.

Chinese Journal of Neuroscience, Mar. 2004, vol. 20, No. 2, pp. 171-173 with English translation.

Akahori, et al., GenBank: "BAC01733.1, "Immunoglobulin kappa light chain VLJ region, partial [*Homo sapiens*], Jul. 2, 2002, 1 pp.

Pascual, V., et al., GnBank: AAA51016.1 cold agglutinin FS-1 L-chain, partial [*Homo sapiens*], Apr. 17, 2013, 1 pp.

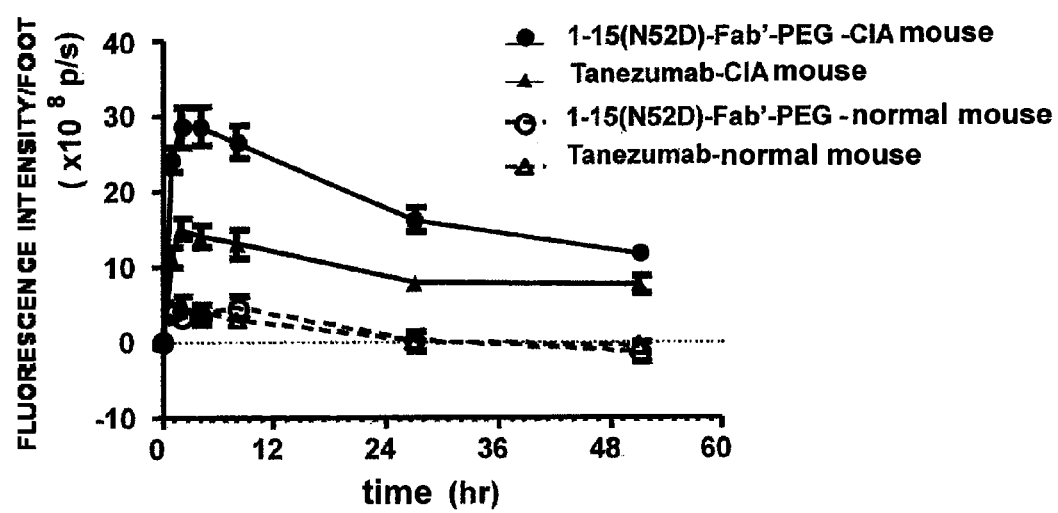

ANTI-HUMAN NGF ANTIBODY

CROSS REFERENCE TO RELATED APPLICATION

This application is a National Stage entry under 35 USC 371 of PCT/JP 2012/070433, filed on Aug. 10, 2012, and herein incorporated in its entirety by reference. Furthermore, this application claims priority to Japanese Patent Application No. 2011-176209 filed on Aug. 11, 2011 and Japanese Patent Application No. 2011-269215 filed on Dec. 8, 2011, both of which are herein incorporated in their entirety by reference.

TECHNICAL FIELD

The present invention relates to a novel anti-human NGF antibody. More specifically, the present invention relates to a Fab' fragment of an anti-human NGF antibody.

BACKGROUND ART

A nerve growth factor (NGF) is one of humoral factors called generally "neurotrophic factors", and plays an important role in generation and differentiation of neurons and in maintaining functions of neurons in the body. As NGF receptors, a high affinity trkA receptor (receptor-type tyrosine kinase) and a low affinity p75NTR receptor are known. There is a report reporting that among these, the p75NTR binds to all of the neurotrophic factors and is involved in apoptosis in the process of neuronal generation. However, the role of the p75NTR has not yet been sufficiently explained. Meanwhile, it is known that knockout mice of the NGF and the trkA receptor express the same phenotype (Non-Patent Document 1), and it is considered that the physiological action of NGF is expressed mainly via the trkA receptor.

In 1993, there was a report reporting that the administration of NGF to rats induced pain (Non-Patent Document 2), and since then, there has been a report reporting that intravenous administration of NGF to human beings induces systemic myalgia and that topical administration of NGF exerts a systemic effect and induces hyperpathia and allodynia in an injection site (Non-Patent Document 3). In addition, there is a report reporting that a knockout mouse of the trkA receptor shows analgesia (Non-Patent Document 4), so it is considered that NGF is a molecule deeply involved in the expression of pain. Regarding the correlation between NGF and the pathological condition of human pain, it has been demonstrated that expression of NGF/trkA is accelerated in articular cartilages with osteoarthritis (OA) (Non-Patent Document 6) and that the level of NGF is increased in patients with rheumatoid arthritis (Non-Patent Document 7) or interstitial cystitis (Non-Patent Document 8).

From the above facts, it is expected that if a monoclonal antibody which specifically binds to NGF and has an inhibitory activity against the action of NGF can be developed, this will be useful for treating, preventing, and diagnosing various diseases including pain relating to NGF.

As anti-human NGF antibodies which have been clinically developed so far, tanezumab (Patent Document 1) and PG110 (Patent Document 2) as humanized anti-human NGF antibodies, and REGN475 (Patent Document 3), fulranumab (Patent Document 4), and MEDI-578 (Patent Document 5) as fully human anti-human NGF antibodies have been reported. Among these, tanezumab is being most briskly developed by priority, and there is a report reporting that according to clinical test results, this antibody exerts a potent and extensive analgesic effect on pain such as arthralgia accompanied by osteoarthritis, chronic back pain, and cystalgia accompanied by interstitial cystitis (Non-Patent Documents 9 to 11).

Generally, as main factors determining an effective dose of an antibody drug, the neutralizing activity of an antibody against an antigen and the amount of antigens present in the body are exemplified. Improving the neutralizing activity leads to the decrease of dose, and consequently, this can be mentioned as very useful amelioration leading to decrease in the financial burden of patients and medical costs. If the decrease in dose can be realized, subcutaneous administration can also be carried out. Subcutaneous administration has a major advantage that a patient can perform self-injection at home if certain conditions are satisfied. In addition, while the antibody drug is generally administered via drips for a certain time in many cases in the intravenous administration, the drug can be administered as a bolus in the subcutaneous administration, which is another advantage. Both the physician and the patient can select a preparation for intravenous administration and a preparation for subcutaneous administration, and this is a desirable factor. However, in the subcutaneous administration, a dose that can be given per administration is as small as about 1 mL in general, so a sufficient amount of antibodies need to be included in the dose so as to express the drug efficacy. Moreover, unlike the intravenous administration, bioavailability needs to be considered for the subcutaneous administration. That is, in order to realize a preparation for subcutaneous administration, it is required to prepare an antibody which exhibits excellent solubility and expresses a sufficient drug efficacy even at a small dose. Accordingly, if an antibody which has a higher neutralizing activity against NGF compared to the antibodies in the related art is obtained, this will be useful for treating diseases relating to NGF and for improving convenience of the treatment.

As described above, though NGF is an important factor for growth of neurons, performing sufficient examination in terms of safety is necessary in developing medical drugs that inhibit the function of NGF. Particularly, as one of the respects which should be examined in terms of safety, the effects on a fetus are exemplified. So far, regarding the functional inhibition of NGF, there have been reports reporting that NGF mutation is the cause of congenital analgesia (Non-Patent Document 5), and that in an animal experiment, when a pregnant guinea pig is caused to produce an autoantibody to NGF so as to inhibit NGF in the body, the newborn guinea pig shows symptoms of analgesia (Non-Patent Document 12). Moreover, in a test using NGF- or trkA-deficient mice, it has been demonstrated that deficiency of NGF action inhibits the growth of neurons of sensory nerves and sympathetic nerves in an embryo (Non-Patent Documents 4 and 13). From these results, it is understood that NGF is an essential factor of neurodevelopment in the early stage of development. The NGF-related diseases also include diseases that women at a child-bearing age suffer from at a high rate, such as interstitial cystitis (half or more of the patients are 44 years old or younger, and 90% of patients are females (Non-Patent Document 14)), chronic back pain (an average age of 40 to 50, and over 50% of patients are females (Non-Patent Documents 15 to 17)), and migraine (a peak age of onset ranges from 15 to 40 years, and 80% of patients are female (Non-Patent Document 18)). In this situation, in developing the anti-NGF antibody as a medical drug, it is very important to avoid the risk of side effects on a fetus in pregnant women.

As another risk factor in a case of developing the anti-NGF antibody as a medical drug, immunocomplex (IC) formation is exemplified. The immunocomplex which is a combination of an antigen and an antibody is generally treated in a reticuloendothelial system such as the spleen or the liver. However, it has been reported that when a pathological condition such as immune abnormality is caused or when the size of the formed IC is large, the IC loses solubility, which relates to the increase of the risk of thrombus formation and to the onset of nephritis caused by the glomerular accumulation of the IC. Though IgG is a bivalent antibody, when an antigen is polyvalent, the IC may have various sizes due to lattice formation. The size of the IC depends on the amount of an antibody and an antigen and the ratio therebetween, affinity of an antibody, and the like. For example, an anti-VEGF antibody bevacizumab (product name: Avastin) is an IgG1 antibody, and there is a report reporting that this antibody forms an IC by binding to a dimer VEGF and induces thrombus formation. Specifically, when Avastin and VEGF are administered to a human FcγRIIα receptor Tg mouse, formation of a pulmonary artery thrombus is observed (Non-Patent Document 19). In addition, there is a report reporting that an arterial thrombus is formed at a higher rate in patients with metastatic cancer who receive chemotherapy with Avastin treatment, compared to a placebo group receiving only chemotherapy (Non-Patent Document 20). Since NGF also forms a dimer in the body to exert physiological activity, it is desirable to further improve safety by avoiding the risk of IC formation in developing a medical drug of the anti-NGF antibody.

For the above reasons, for treating or preventing various NGF-related diseases, it is very important to obtain an anti-NGF antibody which is excellent in safety by reducing the risk of side effects such as the effects on a fetus and thrombus formation while maintaining a high neutralizing activity.

RELATED ART

Patent Document

[Patent Document 1] WO2004/058184
[Patent Document 2] WO2005/061540
[Patent Document 3] WO2009/023540
[Patent Document 4] WO2005/019266
[Patent Document 5] WO2006/077441

Non-Patent Document

[Non-Patent Document 1] Conover J C, et al, Rev Neurosci. 1997, 8:13-27.
[Non-Patent Document 2] Lewin G R, et al, J. Neurosci. 1993, 13:2136-48.
[Non-Patent Document 3] Petty B G, et al, Ann Neurol. 1994, 36:244-6.
[Non-Patent Document 4] Smeyne R J, et al, Nature. 1994, 368:246-9.
[Non-Patent Document 5] Indo Y, et al, Nat. Genet. 1996, 13:485-8.
[Non-Patent Document 6] Iannone F, et al, Rheumatology 2002, 41:1413-8.
[Non-Patent Document 7] Aloe L, et al, Clin Exp Rheumatol. 1997, 15:433-8.
[Non-Patent Document 8] Lowe E M, et al, Br J. Urol. 1997, 79:572-7.
[Non-Patent Document 9] Lane N E, et al, N Engl J. Med. 2010, 363:1521-31.
[Non-Patent Document 10] Evans R J, et al, J. Urol. 2011, 185:1716-21.
[Non-Patent Document 11] Katz N, et al, Pain. 2011, in press
[Non-Patent Document 12] Johnson E M Jr, et al, Science. 1980, 210:916-8.
[Non-Patent Document 13] Crowley C, et al, Cell. 1994, 76:1001-11.
[Non-Patent Document 14] Payne C K, et al, J. Urol. 2007, 177:2042-9.
[Non-Patent Document 15] Manchikanti L, et al, Pain Physician. 2010, 13:E279-92.
[Non-Patent Document 16] Wilkens P, et al, JAMA. 2010, 304:45-52.
[Non-Patent Document 17] Buynak R, et al, Expert Opin Pharmacother. 2010, 11:1787-804.
[Non-Patent Document 18] Sakai F, et al, Cephalalgia. 1997, 17:15-22.
[Non-Patent Document 19] Meyer T, et al, J Thromb Haemost. 2009, 7:171-81.
[Non-Patent Document 20] Scappaticci F A, et al, J Natl Cancer Inst. 2007, 99:1232-9.

SUMMARY OF INVENTION

Technical Problem

An object of the present invention is to provide an anti-human NGF antibody or an antigen-binding fragment thereof that is excellent in safety by reducing the risk of side effects such as effects on a fetus and thrombus formation while maintaining high neutralizing activity.

Solution to Problem

The present invention includes the following invention as medically or industrially useful substances and methods.

[1] An anti-human NGF antibody Fab' fragment comprising:
a heavy-chain variable region consisting of an amino acid sequence shown by SEQ ID NO:6; and
a light-chain variable region consisting of an amino acid sequence shown by SEQ ID NO:4

[2] The Fab' fragment according to [1], wherein a heavy-chain constant region of the Fab' fragment is a human Igγ1 constant region.

[3] The Fab' fragment according to [1], wherein a light-chain constant region of the Fab' fragment is a human Igκ constant region.

[4] The Fab' fragment according to [1], wherein the heavy-chain constant region of the Fab' fragment is the human Igγ1 constant region, and the light-chain constant region of the Fab' fragment is the human Igκ constant region.

[5] The Fab' fragment according to [1], comprising:
a heavy-chain fragment consisting of an amino acid sequence shown by SEQ ID NO:10, SEQ ID NO:14, or SEQ ID NO:16; and
a light chain consisting of an amino acid sequence shown by SEQ ID NO:12.

[6] The Fab' fragment according to any one of [1] to [5], wherein the Fab' fragment is conjugated to polyethylene glycol.

[7] A polynucleotide comprising a sequence that encodes the heavy-chain fragment of the Fab' fragment according to any one of [1] to [6].

[8] A polynucleotide comprising a sequence that encodes the light chain of the Fab' fragment according to any one of [1] to [6].

[9] An expression vector comprising the polynucleotide according to [7] and/or [8].

[10] A host cell transformed with the expression vector according to [9].

[11] The host cell according to [10], which is selected from a group consisting of the following (a) and (b), (a) a host cell transformed with an expression vector comprising a polynucleotide comprising a sequence that encodes the heavy-chain fragment of the Fab' fragment according to any one of [1] to [6] and a polynucleotide comprising a sequence that encodes the light chain of the Fab' fragment; and (b) a host cell transformed with an expression vector comprising a polynucleotide comprising a sequence that encodes the heavy-chain fragment of the Fab' fragment according to any one of [1] to [6] and with an expression vector comprising a polynucleotide comprising a sequence that encodes the light chain of the Fab' fragment.

[12] A method of producing the anti-human NGF antibody Fab' fragment according to any one of [1] to [6], comprising expressing an anti-human NGF antibody Fab' fragment by culturing the host cell according to [10] or [11].

[13] An agent for treating pain, which comprises the Fab' fragment according to any one of [1] to [6].

[14] The agent for treating pain according to [13], wherein the pain is osteoarthritis pain.

[15] A method for preventing or treating pain, comprising administering the Fab' fragment according to any one of [1] to [6].

[16] The method according to [15], wherein the pain is osteoarthritis pain.

[17] The Fab' fragment according to any one of [1] to [6] for use in preventing or treating pain.

[18] The Fab' fragment according to [17], wherein the pain is osteoarthritis pain.

Advantage Effects of the Invention

The anti-human NGF antibody Fab' fragment of the present invention is useful for preventing or treating various diseases in which human NGF is involved in the formation of pathological conditions. Due to its high neutralizing activity, the anti-human NGF antibody Fab' fragment of the present invention brings about excellent improvement in clinical applications, such as decreases in dose, widening of administration intervals, and improvement of the method of administration (for example, a subcutaneous injection). Moreover, in reducing the risk of side effects such as the effects on a fetus and thrombus formation, the anti-human NGF antibody Fab' fragment of the present invention is significantly excellent in terms of safety and greatly contributes to the prevention or treatment of various diseases in which human NGF is involved in the formation of pathological conditions.

BRIEF DESCRIPTION OF THE DRAWINGS

FIG. 1 shows temporal change in the amount of an antibody retained in the sole of a collagen-induced arthritis mouse model.

DESCRIPTION OF EMBODIMENTS

Hereinbelow, the present invention will be described in detail.

The present inventors repeated creative examination to prepare an anti-human NGF antibody or an antigen-binding fragment thereof. As a result, they succeeded in preparing an anti-human NGF antibody Fab' fragment which is excellent in safety by reducing the risk of side effects such as the effects on a fetus and thrombus formation while maintaining high neutralizing activity.

The basic structure of an antibody molecule is common among the respective antibody classes and is constituted with a heavy chain having a molecular weight of 50000 to 70000 and a light chain having a molecular weight of 20000 to 30000. The heavy chain generally consists of a polypeptide chain including about 440 amino acids, and each class has its characteristic structure. The heavy chains are called $\gamma$, $\mu$, $\alpha$, $\delta$, and $\epsilon$ chains corresponding to IgG, IgM, IgA, IgD, and IgE. Furthermore, IgG has subclasses such as IgG1, IgG2, IgG3, and IgG4, and these chains are called $\gamma 1$, $\gamma 2$, $\gamma 3$, and $\gamma 4$ respectively. A light chain generally consists of a polypeptide chain including about 220 amino acids, and two types of the light chain including an L-type and a K-type light chains are known, which are called $\lambda$ and $\kappa$ chains respectively. Regarding the peptide constitution of the basic structure of an antibody molecule, two homologous heavy chains and two homologous light chains are bound via disulfide bonds (S—S bonds) and non-covalent bonds, and the molecular weight thereof is 150000 to 190000. The two kinds of light chains can be paired with any heavy chain. Each antibody molecule always consists of two identical light chains and two identical heavy chains.

There are four intrachain S—S bonds in a heavy chain (five bonds for $\mu$ and $\epsilon$ chains) and two in a light chain. One loop is formed per 100 to 110 amino acid residues, and this steric structure is similar among the respective loops and is called a structural unit or a domain. For both heavy chains and light chains, the amino acid sequence of the domain positioned at the N-terminal thereof is not constant, even in a reference standard from the same class (subclass) of the same animal species, and this domain is called the variable region. Each of the domains is called a heavy-chain variable region ($V_H$) and a light-chain variable region ($V_L$) respectively. Since the amino acid sequence of the C-terminal side from the domain is almost constant in each class or subclass, this region is called a constant region, and each of the domains is described as $C_H 1$, $C_H 2$, $C_H 3$ and $C_L$, respectively.

The antigenic determinant site of an antibody is constituted with $V_H$ and $V_L$, and the binding specificity depends on the amino acid sequence of this site. On the other hand, biological activities such as binding to complements or various cells reflect the differences in the constant region structure among the various classes of Ig. It is known that the variability in the variable regions of the heavy chain and light chain is mostly limited to three small hypervariable regions present in both chains, and these regions are called complementarity determining regions (CDRs; CDR1, CDR2 and CDR3 starting from the N-terminal side). The remaining portion of the variable region is called a framework region (FR) and is relatively constant.

A region between the $C_H 1$ domain and the $C_H 2$ domain of the heavy-chain constant region of an antibody is called a hinge region. This region includes lots of proline residues and has a plurality of inter-chain S—S bonds connecting two heavy-chains. For example, each hinge region of human IgG1, IgG2, IgG3, and IgG4 includes 2, 4, 11, and 2 cysteine residues respectively which constitute the inter-heavy-chain S—S bonds. The hinge region is a region highly sensitive to a proteolytic enzyme such as papain or pepsin. When an antibody is digested with papain, its heavy chain is cleaved at a position closer to the N-terminal side than to the inter-heavy-chain S—S bond of the hinge region, whereby the antibody is broken down into two Fab fragments and one Fc fragment. The Fab fragment is constituted with a light-chain and a heavy-chain fragment including a heavy-chain variable region ($V_H$), a $C_H 1$ domain, and a portion of the hinge region. When an antibody is digested with pepsin, its heavy-chain is cleaved at a position closer to the C-terminal side than to the inter-heavy-chain S—S bond of the hinge region, whereby F(ab')$_2$ fragments is generated. The F(ab')$_2$ fragment is a fragment having a dimeric structure in which two Fab' fragments bind to each other via the inter-heavy-chain S—S bond in the hinge region. The Fab' fragment is constituted with a light-chain and a heavy-chain fragment including a heavy-chain variable region ($V_H$), a $C_H1$ domain, and a portion of the hinge region. Cysteine residues constituting the inter-heavy-chain S—S bond are included in the portion of the hinge region. All of the Fab fragment, F(ab')$_2$ fragment, and Fab' fragment include the variable region and have antigen-binding activity.

The anti-human NGF antibody Fab' fragment of the present invention that the present inventors successfully prepared is a Fab' fragment having the following characteristics.

The anti-human NGF antibody Fab' fragment comprises a heavy-chain variable region consisting of an amino acid sequence shown by SEQ ID NO:6 and a light-chain variable region consisting of an amino acid sequence shown by SEQ ID NO:4.

Specifically, the present inventors constructed antibodies using a human monoclonal antibody development technology, "VelocImmune" mouse [VelocImmune antibody technology; Regeneron Inc. (U.S. Pat. No. 6,596,541)], and screened the antibodies using tests for various biological activities and physical properties, thereby succeeding in identifying the anti-human NGF antibody Fab' fragment of the present invention. In the VelocImmune technology, transgenic mice in which the endogenous immunoglobulin heavy and light chain variable regions are replaced with the corresponding human variable regions are challenged with the antigen of interest (for example, human βNGF), and lymphatic cells are recovered from the mice that express antibodies. The lymphatic cells are fused with mouse myeloma cells to prepare hybridomas. The hybridoma cells are screened to identify hybridoma cells that produce those antibodies that specifically bind to the antigen of interest. The antibodies that are produced herein are antibodies having the variable regions of human antibodies and the constant regions of mouse antibodies (also referred to as chimeric antibodies). Then, if the antibody that binds specifically to the antigen of interest and has a desired neutralizing activity is identified, DNAs that encode the variable regions of the heavy chain and light chain of the antibody are isolated from the hybridoma cells and linked to DNAs encoding the constant regions of the heavy chain and light chain of a desired class of human antibody. The resulting gene encoding the heavy chain and light chain of the antibody is expressed in cells (e.g., CHO cells) to produce an antibody molecule. The heavy chain and light chain of the antibody produced by the above method are the heavy chain and light chain of a "fully human" antibody derived from a human immunoglobulin gene.

The anti-human NGF antibody Fab' fragment of the present invention can be easily prepared by those skilled in the art on the basis of the sequence information on the heavy-chain variable region and light-chain variable region thereof disclosed herein, using a method commonly known in the art. Preferably, the anti-human NGF antibody Fab' fragment of the present invention can be prepared as a fully human antibody Fab' fragment by linking the heavy-chain variable region and light-chain variable regions thereof to a part of the heavy-chain constant region (which includes $C_H1$ domain and a part of hinge region including hinge region cysteine) and light-chain constant region of a human antibody, respectively. Specifically, a heavy-chain variable region gene fragment having a base sequence that encodes the heavy-chain variable region amino acid of the Fab' fragment of the present invention (SEQ ID NO:6), and a light-chain variable region gene fragment having a base sequence that encodes the light-chain variable region amino acid of the Fab' fragment of the present invention (SEQ ID NO:4) are prepared. Then, the variable region genes of the heavy chain and light chain are linked to each gene of a part of heavy-chain constant region and a light-chain constant region in an appropriate class of human antibody to prepare a fully human antibody Fab' fragment gene. Next, this gene is linked to an appropriate expression vector and introduced into a cultured cell. Finally, this cultured cell is cultured, whereby a monoclonal Fab' fragment can be obtained from the culture supernatant.

The gene fragments that encode the heavy-chain and light-chain variable region amino acids of the Fab' fragment of the present invention can be synthesized using a gene synthesis method known in the art, on the basis of, for example, base sequences designed based on the amino acid sequences of the heavy-chain variable region and the light-chain variable region. Examples of this gene synthesis method include various methods known to those skilled in the art, such as the antibody gene synthesis method described in WO90/07861.

Then, the above-described variable region gene fragments are linked to the constant region gene of a human antibody to prepare a fully human Fab' fragment gene. Although any subclass of the constant region (for example, the constant region of a heavy chain such as the γ1, γ2, γ3 or γ4 chain, or the constant region of a light chain such as the λ or κ chain) can be chosen as the constant region of the human antibody, human Igγ1 as the heavy-chain constant region, and human Igκ as the light-chain constant region, can preferably be used.

Subsequent to the preparation of this fully human antibody Fab' fragment gene, introduction of the gene into an expression vector, introduction of the expression vector into cultured cells, cultivation of the cultured cells, purification of the Fab' fragment and the like can be performed using various methods known in the art.

Examples of the expression vector that is linked to thus obtained gene include GS vector pEE6.4 or pEE12.4 (Lonza Biologics), but are not specifically limited, so long as they can express such antibody gene. Also, an expression vector already having a human Ig constant region gene such as AG-γ1 or AG-κ (for example, see WO94/20632) may be used.

The above-described expression vector is introduced into cultured cells by, for example, a calcium phosphate method or an electroporation method and the like.

Examples of the cultured cells into which the expression vector is introduced include cultured cells such as CHO-K1SV cells, CHO-DG44 cells and 293 cells, and these cells may be cultured by a conventional method.

The Fab' fragment accumulated in a culture supernatant after culturing described above can be purified by various types of column chromatography. For example, it is possible to use column chromatography using KappaSelect or the like.

The Fab' fragment of the present invention can be prepared using a recombinant expression method as described above. However, the Fab' fragment may be prepared by performing pepsin digestion after preparing a full-length antibody first, and treating the obtained F(ab')$_2$ fragment with a reductant such as 2-mercaptoethanol.

Preferably, the anti-human NGF antibody Fab' fragment of the present invention can be easily obtained by synthesizing DNA comprising a base sequence encoding the heavy-chain variable region amino acid sequence shown by SEQ ID NO:6 and DNA comprising a base sequence encoding the light-chain variable region amino acid sequence shown by SEQ ID NO:4, and linking the DNAs to a suitable class of human antibody constant region genes, preferably a human Igγ1 constant region gene for the heavy chain and a human Igκ constant region gene for the light chain, to construct a fully human antibody Fab' fragment gene by using a method known in the art, and introducing the gene into an expression vector, introducing the expression vector into a cultured cell, culturing the cultured cell, and purifying an Fab' fragment harvested from the cultured cell by using various methods known in the art. Preferably, DNA comprising a base sequence encoding the heavy-chain variable region amino acid sequences shown by SEQ ID NO:6 comprises the base sequences shown by SEQ ID NO:5. Preferably, DNA comprising a base sequence encoding the light-chain variable region amino acid sequences shown by SEQ ID NO:4 comprises the base sequences shown by SEQ ID NO:3.

In the present specification, the "Fab' fragment" refers to a monovalent antibody fragment constituted with a light-chain and a heavy-chain fragment including a heavy-chain variable region ($V_H$), a $C_H1$ domain, and a portion of a hinge region. In the portion of the hinge region, at least one cysteine residue (also called a "hinge region cysteine" in the present specification) other than cysteine residues constituting the S—S bond between the heavy chain and the light chain is included. The hinge region cysteine can be used as a modification site of polyethylene glycol described later. The number of the hinge region cysteines in the Fab' fragment is variable within a range of from 1 to several cysteine residues depending on the class of an antibody used, and is easily adjustable by a person skilled in the art. For example, when a Fab' fragment of a human IgG1 class (generally having two hinge region cysteines in a hinge region) is prepared, a stop codon is inserted between a coding site of the first hinge region cysteine and a coding site of the second hinge region cysteine in the hinge region of the heavy chain, whereby a Fab' fragment having one hinge region cysteine in the hinge region can be prepared. In addition, if a stop codon is inserted after the coding site of the second hinge region cysteine, a Fab' fragment having two hinge region cysteines in the hinge region can be prepared.

The preferable heavy-chain fragment of the anti-human NGF antibody Fab' fragment of the present invention, comprising the heavy-chain variable region consisting of the amino acid sequence shown by SEQ ID NO:6 and a portion of a human Igγ1 constant region, is a heavy-chain fragment consisting of the amino acid sequence shown by SEQ ID NO:10, SEQ ID NO:14, or SEQ ID NO:16. Preferably, DNA comprising a base sequence that encodes the heavy-chain fragment of the anti-human NGF antibody Fab' fragment consisting of the amino acid sequence shown by SEQ ID NO:10, SEQ ID NO:14, or SEQ ID NO:16 comprises the base sequence shown by SEQ ID NO:9, SEQ ID NO:13, or SEQ ID NO:15. The preferable light chain of the anti-human NGF antibody Fab' fragment of the present invention, comprising the light-chain variable region consisting of the amino acid sequence shown by SEQ ID NO:4 and a human Igκ constant region, is a light chain consisting of the amino acid sequence shown by SEQ ID NO:12. Preferably, DNA comprising a base sequence that encodes the light chain of the anti-human NGF antibody Fab' fragment consisting of the amino acid sequence shown by SEQ ID NO:12 comprises the base sequence shown by SEQ ID NO:11.

As a preferable anti-human NGF antibody Fab' fragment of the present invention that comprises the heavy-chain fragment consisting of the amino acid sequence shown by SEQ ID NO:10 and the light-chain consisting of the amino acid sequence shown by SEQ ID NO:12, a fully human 1-15 (N52D) antibody Fab' fragment described later in examples is exemplified. As a preferable anti-human NGF antibody Fab' fragment of the present invention that comprises the heavy-chain fragment consisting of the amino acid sequence shown by SEQ ID NO:14 and the light chain consisting of the amino acid sequence shown by SEQ ID NO:12, a fully human 1-15 (N52D-A) antibody Fab' fragment described later in examples is exemplified. As a preferable anti-human NGF antibody Fab' fragment of the present invention that comprises the heavy-chain fragment consisting of the amino acid sequence shown by SEQ ID NO:16 and the light chain consisting of the amino acid sequence shown by SEQ ID NO:12, a fully human 1-15(N52D-P) antibody Fab' fragment described later in examples is exemplified.

The present invention also comprises an anti-human NGF antibody Fab' fragment that comprises the heavy-chain variable region comprising CDR1 consisting of amino acid sequence at position from 31 to 35 of SEQ ID NO: 6, CDR2 consisting of amino acid sequence at position from 50 to 65 of SEQ ID NO: 6, and CDR3 consisting of amino acid sequence at position from 98 to 110 of SEQ ID NO: 6, and the light-chain variable region comprising CDR1 consisting of amino acid sequence at position from 24 to 39 of SEQ ID NO: 4, CDR2 consisting of amino acid sequence at position from 55 to 61 of SEQ ID NO: 4, and CDR3 consisting of amino acid sequence at position from 94 to 102 of SEQ ID NO: 4. The Fab' fragment can be also prepared by those skilled in the art according to procedures such as ones described above.

The anti-human NGF antibody Fab' fragment of the present invention may be modified by being conjugated to polyethylene glycol (PEG) via the hinge region cysteine thereof. PEG can be conjugated to the Fab' fragment by using methods known in the art (for example, EP0948544). In the present invention, linear or branched PEG having an arbitrary average molecular weight or a derivative thereof is usable, which can be easily selected by a person skilled in the art according to the intended use. For example, in a tumor tissue or at the time of inflammatory response, vascular permeability is markedly enhanced compared to a normal tissue, so substances reaching the tissue tend to leak out of the blood vessel and accumulate in the tumor or the inflammatory tissue (EPR effect). It is also known that a low molecular weight substance is easily reabsorbed into blood vessels and that a high molecular weight substance is not easily reabsorbed. Therefore, in order to improve retentivity of the Fab' fragment in a lesional tissue, PEG having a high average molecular weight (for example, about 40000 Da) may be conjugated to this fragment. When the Fab' fragment is desired to be rapidly excreted outside the body, PEG having a low average molecular weight (for example, about 10000 Da) may be conjugated to this fragment. Moreover, in order to facilitate the binding of PEG to the hinge region cysteine, a PEG derivative may be used. For example, as described later in examples, it is possible to use a PEG derivative to which a thiol-reactive group such as maleimide has been bound and bind a thiol group of the hinge region cysteine to the maleimide group via a covalent bond. Generally, the average molecular weight of PEG ranges from about 500 Da to about 50000 Da, preferably ranges from about 5000 Da to about 40000 Da and more preferably ranges from about 10000 Da to about 40000 Da.

The anti-human NGF antibody Fab' fragment of the present invention binds to human NGF. As the method of measuring binding activity of the obtained anti-human NGF antibody Fab' fragment to the human NGF, there is a method such as ELISA or FACS. For example, when ELISA is used, human βNGF is immobilized in an ELISA plate, the Fab' fragment is added thereto to cause a reaction, and then a secondary antibody such as an anti-kappa antibody labeled with an enzyme such as horseradish peroxidase (HRP) is allowed to react with the reaction mixture. After the plate is washed, the activity is measured by using a reagent (for example, a TMB chromogenic reagent in a case of HRP labeling) detecting the activity, thereby identifying binding of the secondary antibody. In addition, the anti-human NGF antibody Fab' fragment of the present invention also includes a Fab' fragment that binds to NGF derived from another animal (for example, mouse NGF) as well as human NGF, so binding activity with respect to such a protein may be measured.

The anti-human NGF antibody Fab' fragment of the present invention has neutralizing activity with respect to human NGF. When being used in the present specification, the term "neutralizing activity" of the anti-human NGF antibody Fab' fragment refers to an activity that inhibits any biological activity resulting from NGF by binding to NGF, and the neutralizing activity can be evaluated using one or a plurality of biological activities of NGF as an index. Examples of such neutralizing activity include the inhibitory activity against binding of NGF to trkA which is the NGF receptor, the inhibitory activity against intracellular calcium influx mediated by an NGF-trkA signal, and the inhibitory activity against NGF-dependent cell survival signaling. The neutralizing activity can be evaluated using methods described later in examples.

In order to more specifically evaluate the effect of the anti-human NGF antibody Fab' fragment of the present invention, an in vivo test may be performed. For example, as described later in examples, the in vivo drug efficacy of the Fab' fragment can be evaluated by an analgesic effect test or the like that uses a mouse arthritis model. It is also possible to evaluate the retention effect in a lesional tissue by using a test for distribution property into a lesion.

Further, the anti-human NGF antibody Fab' fragment of the present invention may also be evaluated in terms of the risk of side effects. For example, as described later in examples, by using a placental transfer test performed after administration of the Fab' fragment to pregnant animals, it is possible to evaluate the possibility that the anti-human NGF antibody Fab' fragment of the present invention may exert effects on a fetus. In addition, as described later in examples, the size of an immunocomplex (IC) formed between the anti-human NGF antibody Fab' fragment of the present invention and NGF is measured by using a test for IC formation with NGF, whereby the possibility of the induction of thrombus formation can be evaluated.

In addition, as the method of evaluating various types of stability (for example, thermal stability, long-term storage stability, and high-concentration stability) of the anti-human NGF antibody Fab' fragment of the present invention, a method of using differential scanning calorimetry and a method of measuring the formation of aggregates during storage are exemplified.

The anti-human NGF antibody Fab' fragment of the present invention is optionally purified and then formulated according to common methods, and can be used for treating pain such as osteoarthritis pain (OA pain), rheumatic pain, cancer pain, neuropathic pain, chronic low back pain, postoperative pain, postherpetic neuralgia, painful diabetic neuropathy, fracture pain, and painful bladder syndrome and diseases in which NGF is involved in the formation of pathological conditions, such as interstitial cystitis, acute pancreatitis, chronic pancreatitis, and endometriosis.

The anti-human NGF antibody Fab' fragment of the present invention can be used preferably as an agent for treating pain and more preferably as an agent for treating osteoarthritis pain. Examples of the formulation of this treating agent and the like include parenteral formulations such as injectable agents and infusion agents, which are preferably administered by intravenous administration, subcutaneous administration and the like. In the formulation process, carriers or additives that match these formulations can be used within a pharmaceutically acceptable range.

The amount of inventive anti-human NGF antibody Fab' fragment added in the above-described formulation varies depending on the patient's symptom severity or age, the dosage form of the formulation used or the binding titer of the antibody and the like; for example, about 0.001 mg/kg to 100 mg/kg of the antibody may be used.

The present invention also provides a polynucleotide comprising a sequence encoding the anti-human NGF antibody Fab' fragment of the present invention, and an expression vector comprising the same. The present invention also provides a polynucleotide comprising a sequence encoding the heavy-chain variable region of the anti-human NGF antibody Fab' fragment of the present invention, and a polynucleotide comprising a sequence encoding the light-chain variable region of the anti-human NGF antibody Fab' fragment of the present invention, and expression vector comprising either or both of them. The expression vector of the present invention is not specifically limited, so long as it can express a gene that encodes the Fab' fragment of the present invention or its heavy-chain variable region and/or light-chain variable region in various host cells of prokaryotic cells and/or eukaryotic cells, and produce these polypeptides. Examples thereof include plasmid vectors, viral vectors (for example, adenovirus, retrovirus) and the like. Preferably, the expression vector of the present invention comprises a polynucleotide comprising either a sequence encoding the heavy chain fragment or light chain fragment of the above-described Fab' fragment of the present invention, or both a polynucleotide comprising a sequence encoding the heavy chain fragment of the Fab' fragment of the present invention and a polynucleotide comprising a sequence encoding the light chain of the Fab' fragment of the present invention.

The expression vector of the present invention can comprise a gene that encodes the anti-human NGF antibody Fab' fragment of the present invention, or a gene that encodes the heavy-chain variable region and/or light-chain variable region of the anti-human NGF antibody Fab' fragment of the present invention, and a promoter operably linked to the gene. Examples of a promoter for expressing a gene encoding the Fab' fragment of the present invention or its heavy-chain variable region and/or light-chain variable region in a bacterium include Trp promoter, lac promoter, recA promoter, λPL promoter, 1pp promoter, tac promoter and the like, when the host is a bacterium of the genus *Escherichia*. Examples of a promoter for expression in yeast include PH05 promoter, PGK promoter, GAP promoter and ADH promoter, and some examples of a promoter for expression in the genus *Bacillus* include SL01 promoter, SP02 promoter, penP promoter and the like. When the host is a eukaryotic cell such as a mammalian cell, examples of the promoter include SV40-derived promoter, retrovirus promoter, heat shock promoter and the like.

When a bacterium, particularly *Escherichia coli*, is used as the host cell, the expression vector of the present invention can further comprise an initiation codon, a stop codon, a terminator region and a replicable unit. When yeast, an animal cell or insect cell is used as the host, the expression vector of the present invention can comprise an initiation codon and a stop codon. In this case, it may comprise an enhancer sequence, noncoding regions on the 5' side and 3' side of a gene that encodes the Fab' fragment of the present invention or the heavy-chain variable region or light-chain variable region thereof, a secretion signal sequence, a splicing junction, a polyadenylation region, a replicable unit or the like. Also, it may comprise a selection marker that is in common use (for example, tetracycline-resistant gene, ampicillin-resistant gene, kanamycin-resistant gene, neomycin-resistant gene, dihydrofolic acid reductase gene) according to the intended use.

The present invention also provides a transformant introduced with a gene encoding the anti-human NGF antibody Fab' fragment of the present invention or a gene encoding the heavy-chain variable region and/or light-chain variable region of the anti-human NGF antibody Fab' fragment of the present invention. Such a transformant can be prepared by, for example, transforming a host cell with the expression vector of the present invention. A host cell that is used to prepare the transformant is not specifically limited, so long as it is suitable for the aforementioned expression vector and is transformable; examples thereof include various cells such as natural cells or artificially established lines of cells commonly being used in the technical field of the present invention (for example, bacteria (bacteria of the genus *Escherichia*, bacteria of the genus *Bacillus*), yeasts (the genus *Saccharomyces*, the genus *Pichia* and the like), animal cells or insect cells (for example, Sf9) and the like. The transformation can be performed by any known method per se.

Preferably, the transformant of the present invention is either a host cell transformed with an expression vector comprising a polynucleotide comprising a sequence encoding the heavy-chain variable region of the Fab' fragment of the present invention and a polynucleotide comprising a sequence encoding the light-chain variable region of the Fab' fragment, or a host cell transformed with an expression vector comprising a polynucleotide comprising a sequence encoding the heavy-chain variable region of the Fab' fragment of the present invention and an expression vector comprising a polynucleotide comprising a sequence encoding the light-chain variable region of the Fab' fragment. More preferably, the transformant of the present invention is either a host cell transformed with an expression vector comprising a polynucleotide comprising a sequence encoding the heavy chain fragment of the above-described Fab' fragment of the present invention and a polynucleotide comprising a sequence encoding the light chain of the Fab' fragment, or a host cell transformed with an expression vector comprising a polynucleotide comprising a sequence encoding the heavy chain fragment of the above-mentioned Fab' of the present invention and an expression vector comprising a polynucleotide comprising a sequence encoding the light chain of the Fab' fragment.

The present invention also provides a method for producing the anti-human NGF antibody Fab' fragment of the present invention, comprising expressing in a host cell a gene encoding the anti-human NGF antibody Fab' fragment of the present invention or a gene encoding the heavy-chain variable region and/or light-chain variable region of the anti-human NGF antibody Fab' fragment of the present invention, that is, using such a transformant. Preferably, the host cell that is used in the above method is a host cell transformed with the above-described expression vector of the present invention, and it may separately or simultaneously comprise a polynucleotide comprising a sequence encoding the heavy-chain variable region of the Fab' fragment of the present invention and a polynucleotide comprising a sequence encoding the light-chain variable region of the Fab' fragment.

When producing the anti-human NGF antibody Fab' fragment of the present invention, the transformant may be cultured in a nutrient medium. The nutrient medium preferably contains a carbon source and an inorganic nitrogen source or organic nitrogen source, which are required for the growth of the transformant. Examples of the carbon source include glucose, dextran, soluble starch, sucrose and the like; examples of the inorganic nitrogen source or organic nitrogen source include ammonium salts, nitrates, amino acids, corn steep liquor, peptone, casein, meat extract, soybean cake, potato extract and the like. If desired, other nutrients (for example, inorganic salts (for example, calcium chloride, sodium dihydrogen phosphate, magnesium chloride), vitamins, antibiotics (for example, tetracycline, neomycin, ampicillin, kanamycin and the like) and the like) may be contained.

Culture of the transformant is performed by a method known per se. Culture conditions, for example, temperature, pH of the medium, and culture time are suitably selected. For example, when the host is an animal cell, an MEM medium containing about 5% to 20% fetal bovine serum (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like can be used as the medium. The pH of the medium is preferably about 6 to 8, culture is normally performed at about 30° C. to 40° C. for about 15 to 72 hours, and aeration or agitation may be performed as necessary. When the host is an insect cell, for example, Grace's medium comprising fetal bovine serum (Proc. Natl. Acad. Sci. USA, Vol. 82, p. 8404, 1985) and the like can be mentioned, and the pH thereof is preferably about 5 to 8. Culturing is normally performed at about 20° C. to 40° C. for 15 to 100 hours, and aeration or agitation may be performed as necessary. When the host is a bacterium, an *actinomyces*, yeast, or a filamentous fungus, for example, a liquid medium comprising the above-described nutrient sources is appropriate. A medium having a pH of 5 to 8 is preferable. When the host is *E. coli*, preferred examples of the medium include LB medium, M9 medium (Miller et al., Exp. Mol. Genet, Cold Spring Harbor Laboratory, p. 431, 1972) and the like. In this case, culture can be normally performed at 14° C. to 43° C. for about 3 to 24 hours, while aeration or agitation is performed as necessary. When the host is a bacterium of the genus *Bacillus*, cultivation can be normally performed at 30° C. to 40° C. for about 16 to 96 hours, while aeration or agitation is performed as necessary. When the host is yeast, examples of the medium include Burkholder's minimal medium (Bostian, Proc. Natl. Acad. Sci. USA, Vol. 77, p. 4505, 1980), and the pH of the medium is desirably 5 to 8. Culturing is normally performed at about 20° C. to 35° C. for about 14 to 144 hours, and aeration or agitation may be performed as necessary.

The anti-human NGF antibody Fab' fragment of the present invention can be recovered, preferably isolated and purified, from a cultured transformant as described above. Examples of the method of isolation and purification include methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxyl apatite chromatography; methods based on specific affinity, such as affinity chromatography; methods based on differences in hydrophobicity, such as reverse phase high performance liquid chromatography; methods based on differences in isoelectric point, such as isoelectric focusing; and the like.

Although the present invention has been generally described above, specific examples are provided herein only for a better understanding of the present invention. These examples are for illustrative purposes only and do not limit the scope of the present invention.

EXAMPLES

In steps using a commercially available kit or reagent, experiments were performed according to the attached protocols unless otherwise specified.

Example 1

Immunization of VelocImmune Mouse

An anti-human NGF antibody was obtained by immunizing VelocImmune mice. In order to increase diversity of the obtained antibody, the present inventors examined a plurality of immunization methods, routes of administration, adjuvants, immunization periods, and the like. By using a human βNGF (R&D Systems, Inc.) as an immunogen, the present inventors examined a method of immunization in which the human βNGF is used for immunization by mixing it with an adjuvant after dissolution, and a method of immunization in which the human βNGF is used by mixing it with an adjuvant after thermally denaturing (treating at 80° C. for 10 minutes in a 0.5% SDS solution). As the route of administration, footpad administration and intraperitoneal administration were examined. As the adjuvant, TiterMax Gold (CytRx Corporation), complete Freund's Adjuvant (Sigma), incomplete Freund's Adjuvant (Sigma), and RIBI Adjuvant (Corixa Corporation) were examined. As an immunoactivator to be added, CpG oligonucleotide and Aluminum Phosphate Gel (BRENNTAG) were examined. As the immunization period, 3 to 14 weeks were examined. After the animals was immunized several times, blood was collected from the caudal vein of the mice, and the titer was monitored. In this manner, VelocImmune mice producing an antibody binding to the human NGF were selected.

The titer was measured using the following standard ELISA method. The human βNGF was added to a Maxisorp 384 plate (Nunc) at 10 ng/well and immobilized by being incubated overnight at 4° C. The next day, the plate was washed once with a wash solution (TBST: a tris buffer (TBS) containing 0.05% Tween-20), a blocking agent (TBST containing 20% Blocking One (Nacalai Tesque, Inc.)) was then added thereto, and the plate was left to stand at room temperature for an hour. After the plate was washed once with the TBST wash solution, the collected blood was serially diluted and added to the plate. After an hour of incubation at room temperature, the plate was washed three times with the TBST wash solution, and an HRP-goat anti-mouse Ig antibody (Zymed) which was 2000-fold diluted with the TBST wash solution containing 5% Blocking One was added thereto. After an hour of incubation at room temperature, the plate was washed three times with the TBST wash solution. The plate was supplemented with a TMB chromogenic reagent (SUMITOMO BAKELITE CO., LTD) and left to stand at room temperature for 10 minutes, a stop solution (2 mol/L sulfuric acid) was then added thereto to stop the reaction, and an absorbance at 450 nm was measured.

Example 2

Preparation of Anti-Human NGF Antibody-Producing Hybridoma

The mice selected by confirming the increase in antibody titer were finally immunized (intravenous or intraperitoneal administration of an antigen). The spleen, lymph node, or the like of the immunized mice was extracted according to a normal method so as to collect lymphocytes, and the lymphocytes were fused with mouse myeloma cells SP2/0, thereby preparing a hybridoma. The hybridoma was subjected to limiting dilution and monocloning, and the antibody was purified from the supernatant by using a protein A or protein G column (GE Healthcare Japan).

Example 3

Evaluation of NGF-trkA Binding Inhibition

The human βNGF (R&D Systems, Inc.) was allowed to react with EZ-LINK 5-(biotinamido)pentylamine (Pierce) at room temperature for 30 minutes in a dark place to perform biotin labeling, and the excess biotin was removed using a desalting column, thereby obtaining biotin-labeled human βNGF. In the following Examples 6 and 7, the prepared biotin-labeled human βNGF was confirmed to have the same biological activity as that of the original human βNGF.

Inhibitory activity was measured by the following method. The human trkA (R&D Systems, Inc.) was added to a white Maxisorp 384 plate (Nunc) at 60 ng/well and immobilized by being incubated overnight at 4° C. The next day, the plate was washed once with the TBST wash solution, a blocking agent (TBST containing 20% Blocking One (Nacalai Tesque, Inc.)) was then added thereto, and the plate was left to stand at room temperature for an hour. Subsequently, a mixture obtained by mixing the biotin-labeled human βNGF (0.2 μg/ml) prepared as above with the antibody prepared in Example 2 was added to the trkA-immobilized plate having undergone blocking. After an hour of incubation at room temperature, the plate was washed three times with the TBST wash solution, and alkaline phosphatase-labeled streptavidin (Pierce) was added thereto. After an hour of incubation at room temperature, the plate was washed three times with the TBST wash solution and then supplemented with APU4 (BioFx) which is a reagent detecting chemiluminescence, and the amount of chemiluminescence was measured by an EnVision counter (PerkinElmer Co., Ltd.).

Example 4

Evaluation of Species Cross-Reactivity

When an antibody has cross-reactivity with respect to a mouse βNGF, it is possible to perform drug efficacy evaluation in a mouse pathological model by using the antibody. Consequently, a biotin-labeled mouse βNGF was prepared in the method of Example 3 by using a mouse βNGF (R&D Systems, Inc.), whereby the cross-reactivity of the antibody to the mouse βNGF was evaluated.

Example 5

Evaluation of Binding Specificity

The binding specificity of the antibody to NGF was evaluated by using the ELISA method described in Example 1. Specifically, NT-3 as a family molecule showing the highest homology to NGF was used. Human NT-3 (PeproTech) was added to the plate in the method of Example 1 at 20 ng/well and immobilized in the plate, thereby allowing performance of evaluation.

Example 6

Evaluation of NGF-trkA Signaling Inhibition

The inhibitory activity of the antibody against NGF-trkA signaling was evaluated. NGF increases intracellular calcium ($Ca^{2+}$) concentration via trkA as the NGF receptor. Generally, the change in $Ca^{2+}$ concentration can be evaluated in the presence of a calcium indicator by using an intracellular calcium ($Ca^{2+}$) concentration measurement system (FLIPR; Molecular Devices, LLC.).

The inhibitory activity was measured by the following method. HEK293 cells (WO2009/054468) caused to stably express the human trkA were dispensed in a 96-well poly-D-lysine-coated plate (Becton, Dickinson and Company, Japan) at $2\times10^4$ cells/well the day before experiment and cultured overnight. The next day, the culture medium was replaced with a DMEM culture medium (containing 3.6 mM sodium hydroxide (NaOH) and 2.5 mM probenecid (Sigma)) containing a calcium indicator (Fluo4-AM; Dojindo) and left to stand at 37° C. for 30 minutes. Thereafter, the cells were washed twice with a wash solution (Hank's balanced salt solution) (HBSS) (20 mM 2-[4-(2-hydroxyethyl)-1-piperazinyl]ethane sulfonic acid (HEPES), 3.6 mM sodium hydroxide, 2.5 mM probenecid (Sigma), and 0.1% bovine serum albumin), and the culture medium was replaced with this wash solution at 150 μl/well. The cell plate was set in the FLIPR. By operating the FLIPR, a mixed solution of the antibody obtained in Example 2 and NGF was added to the plate at 50 μl/well (final NGF concentration of 100 ng/ml), and the change in intracellular $Ca^{2+}$ concentration was measured. The difference between maximum and minimum values of the change in intracellular $Ca^{2+}$ concentration was calculated and stored as measurement data.

Example 7

Evaluation of NGF-Dependent Cell Survival Signaling Inhibition

When PC 12 cells naturally expressing the trkA and p75 receptors are cultured in a serum-free condition, NGF enables the cells to survive for several days. By the following method, the inhibitory activity of the antibody against the NGF-dependent cell survival signaling was evaluated.

PC 12 cells were seeded in a 96-well collagen-coated plate (ASAHI TECHNO CO., LTD.) at $1\times10^4$ cells/well and incubated overnight in an F12K culture medium (Invitrogen) containing 2.5% fetal bovine serum and 15% inactivated horse serum (Invitrogen) at 37° C. under 5% $CO_2$. The next day, the culture medium was replaced with only F12K in a serum-free condition. After an hour, the antibody and the human βNGF (final concentration of 50 ng/ml) were added thereto, followed by culturing for 72 hours. Subsequently, the culture solution was removed by an aspirator, and cell viability was measured using a reagent (CellTiter Glo; Promega Corporation) quantitating endogenous ATP of cells.

Example 8

Preparation of Fab Fragment

A digestive enzyme papain-bound gel was added to 1 mg/ml of the antibody by using a Fab preparation kit (Pierce), followed by treatment at 37° C. for 3 hours. The treated reaction solution was added to a protein G column (GE Healthcare Japan), cleaved Fc and unreacted IgG were removed by being adsorbed onto the column, and the eluted fraction was collected, thereby obtaining Fab fragments. The obtained Fab fragments were evaluated by the tests described in Examples 3, 6, and 7.

As a result of the evaluation of Examples 3 to 8, it was confirmed that the antibody named 1-15 (chimeric antibody) had high neutralizing activity, species cross-reactivity, and binding specificity and maintained high neutralizing activity even though this antibody is in the form of a monovalent antibody fragment.

Example 9

Determining Antibody Gene Sequence

For the identified antibody 1-15, the present inventors cloned genes encoding the heavy chains and light chains of the antibody from hybridomas. Specifically, a hybridoma clone was prepared in an amount of $1\times10^5$ or more and suspended in RLT buffer which is included in RNeasy Mini Kit (QIAGEN), and then the cells were shredded with QIAshredder (QIAGEN). Subsequently, RNA was extracted according to the protocol, and by using the extracted RNA as a template, cDNA was synthesized using a DNA amplification kit (SMARTer RACE cDNA Amplification Kit; Clontech). PCR was carried out using the obtained cDNA, thereby elongating and amplifying the variable region of the heavy chains and light chains. Sequence analysis was performed directly on the PCR products by using a sequencer (ABI PRISM 3100; Applied Biosystems). In addition, the PCR products were recombined with a PCR product subcloning vector such as pCR3.1-TOPO (Invitrogen), followed by gene sequence analysis, thereby determining the sequence.

The determined base sequence of the heavy-chain variable region of the antibody 1-15 is shown by SEQ ID NO:1, and the amino acid sequence thereof is shown by SEQ ID NO:2. Moreover, the base sequence of the light-chain variable region of the antibody is shown by SEQ ID NO:3, and the amino acid sequence thereof is shown by SEQ ID NO:4. The CDR1, CDR2 and CDR3 of the heavy-chain variable region of the antibody 1-15 is a region of position from 31 to 35, 50 to 65, and 95 to 102 of the heavy-chain variable region based on Kabat numbering, respectively, which consists of the amino acid sequence at position from 31 to 35, 50 to 65, and 98 to 110 of SEQ ID NO:2, respectively. The CDR1, CDR2 and CDR3 of the light-chain variable region of the antibody 1-15 is a region of position from 24 to 34, 50 to 56, and 89 to 97 of the light-chain variable region based on Kabat numbering, respectively, which consists of the amino acid sequence at position from 24 to 39, 55 to 61, and 94 to 102 of SEQ ID NO:4, respectively.

Example 10

Preparation of Mutant of Glycosylation Site of Variable Region

The amino acid (SEQ ID NO:2) of the heavy-chain variable region of the antibody 1-15 described above includes an N-type glycosylation motif sequence as N-X-(T/S). Specifically, in the heavy-chain variable region shown by SEQ ID NO:2, Asn (N52) at position 52 based on Kabat numbering corresponds to the glycosylation site. It is known that though glycosylation of an antibody occurs during cell culturing if the antibody has glycosylation site, the glycosylation depends on the culturing conditions or the host expressing the antibody. In other words, even among the same antibody-producing cells established, the degree of glycosylation is likely to vary with the culturing conditions (such as the culture medium and cell density), which leads to a possibility that it may be difficult to obtain antibody drugs having uniform quality. Therefore, the present inventors prepared 1-15 (N52D) which was obtained by introducing a mutation to N52 in the heavy-chain variable region of the antibody 1-15.

The base sequence of the heavy-chain variable region of the prepared 1-15(N52D) is shown by SEQ ID NO:5, and the amino acid sequence thereof is shown by SEQ ID NO:6. The CDR1, CDR2 and CDR3 of the heavy-chain variable region of the antibody 1-15(N52D) is a region of position from 31 to 35, 50 to 65, and 95 to 102 of the heavy-chain variable region based on Kabat numbering, respectively, which consists of the amino acid sequence at position from 31 to 35, 50 to 65, and 98 to 110 of SEQ ID NO:6, respectively.

Example 11

Preparation of Fully Human Antibody Fab' Fragment

By using the heavy-chain variable regions of 1-15 and 1-15(N52D) described above and the light-chain variable region of 1-15, the respective fully human antibody Fab' fragments were prepared.

A signal sequence was linked to the 5' side of the respective heavy-chain variable region genes of 1-15 and 1-15(N52D), and the constant region gene of human Igγ1 (Man Sung Co. et al., (1992) J. Immunol. Vol. 148(4):1149-1154) was linked to the 3' side thereof respectively. This heavy-chain fragment gene was inserted into GS vector pEE6.4 (Lonza Biologics). At this time, in order to express the genes as a Fab' fragment, a stop codon was inserted after the codon of Cys at position 226 (corresponding to Cys at position 230 in the amino acid sequence of SEQ ID NO:8 and SEQ ID NO:10 described later) based on the EU index in the heavy-chain constant region gene. In addition, a signal sequence was linked to the 5' side of the light-chain variable region gene of 1-15, and the constant region gene of human κ chain (Man Sung Co. et al., described above) was linked to the 3' side thereof respectively. This light-chain gene was inserted into GS vector pEE12.4 (Lonza Biologics).

The Fab' fragment was expressed in two manners including transient expression and constant expression. In the transient expression, FreeStyle 293 cells (Invitrogen) cultured in FreeStyle 293 Expression Medium (Invitrogen) at about 1,000,000 cells/mL were transfected with the above-described GS vectors of the heavy-chain fragment and the light-chain by using 293fectin (Invitrogen), followed by culturing for seven days. In the constant expression, both the GS vectors described above were cleaved with restriction enzymes NotI and PvuI, followed by ligation by using a DNA ligation kit (TAKARA BIO INC), thereby constructing a GS vector into which genes of both the heavy-chain fragment and the light-chain were inserted. This expression vector encodes the heavy-chain fragment, the light chain, and glutamine synthetase and was expressed by being transfected to CHO-K1-SV cells. After the vectors were expressed in the respective manners, the culture supernatant was purified by using KappaSelect (GE Healthcare Japan), thereby obtaining the respective Fab' fragments.

The base sequence of the heavy-chain fragment of the prepared fully human 1-15 antibody Fab' fragment (also referred to as 1-15-Fab') is shown by SEQ ID NO:7, and the amino acid sequence thereof is shown by SEQ ID NO:8 respectively.

The base sequence of the heavy-chain fragment of the prepared fully human 1-15(N52D) antibody Fab' fragment (also referred to as 1-15(N52D)-Fab') is shown by SEQ ID NO:9, and the amino acid sequence thereof is shown by SEQ ID NO:10 respectively.

The light chain of the respective Fab' fragments are the same and the base sequence thereof is shown by SEQ ID NO:11, and the amino sequence thereof is shown by SEQ ID NO:12 respectively.

Example 12

Evaluation of Neutralizing Activity and Expression Level of Fully Human Antibody Fab' Fragment The 1-15-Fab' and the 1-15(N52D)-Fab' obtained in Example 11 were evaluated by the tests described in Examples 3 and 6. In the test of Example 3, IC50 of the 1-15-Fab' and the 1-15(N52D)-Fab' was 0.17 μg/ml and 0.18 μg/ml respectively. In the test of Example 6, IC50 of the 1-15-Fab' and the 1-15(N52D)-Fab' was 0.021 μg/ml and 0.018 μg/ml respectively. From these results, it was confirmed that the neutralizing activity of the 1-15(N52D)-Fab' was maintained to almost the same degree as that of the unmodified 1-15-Fab', and that the neutralizing activity was not influenced even if a mutation was introduced.

In addition, the respective Fab' fragments were expressed by the constant expression, and the amount of antibody produced in the culture supernatant of a stable expression cell pool was measured. As a result, the concentrations of the respective culture supernatants of the 1-15-Fab' and the 1-15 (N52D)-Fab' were 86 mg/L and 106 mg/L respectively, which showed that the 1-15(N52D)-Fab' is an antibody produced in a higher amount than the unmodified 1-15-Fab'.

Example 13

Preparation of PEGylated Fab' Fragment and Evaluation of Neutralizing Activity

Next, the present inventors introduced PEG to the 1-15 (N52D)-Fab'. After being purified by KappaSelect, the Fab' fragment was subjected to a reduction reaction by using TCEP hydrochloride (Tris(2-carboxyethyl)phosphine HCl), whereby the Fab' fragment was made into a PEGylatable structure.

Specifically, TCEP was added to a Fab' fragment solution of which the concentration was adjusted to 1.2 mg/ml by a 20 mM of sodium phosphate buffer (pH 6.8), such that the TCEP became 1 mM, followed by a reaction at 37° C. for 2 hours, and then the resultant was diluted with a 20 mM sodium acetate buffer (pH 5.0) to adjust pH. This solution was adsorbed onto a cation exchange resin (SP-5PW; TOSOH CORPORATION) and subjected to NaCl gradient elution, and the main peak was collected. The obtained Fab' fragment was diluted with a 20 mM sodium phosphate buffer (pH 6.8) so as to yield 1 mg/ml, the pH was adjusted to 6.8, and then the solution was left to stand at 4° C. for a night or longer so as to be naturally oxidized. 40 kDa PEG (SUNBRIGHT GL2-400MA; NOF CORPORATION) was added to the solution to yield a final concentration of 0.1 mM, and the solution was left to stand at room temperature for 2 hours and then at 4° C. overnight. Having a maleimide group on the terminal thereof, this PEG rapidly reacts with Cys (C226 based on EU index; Cys at position 230 of SEQ ID NO:10) of the carboxyl terminal of the heavy-chain fragment. The solution was diluted with a 20 mM sodium acetate buffer (pH 4.5) to adjust pH and then adsorbed again onto a cation exchange resin (SP-5PW; TOSOH CORPORATION), the resultant was subjected to NaCl gradient elution, and the main peak was collected. The resultant PEGylated Fab' fragment was purified. This PEGylated 1-15(N52D)-Fab' is also called 1-15(N52D)-Fab'-PEG.

The neutralizing activity of the non-PEGylated and PEGylated 1-15(N52D)-Fab's was evaluated by the method shown in Example 3. As a result, while IC50 of the 1-15(N52D)-Fab' was 0.15 μg/ml, IC50 of the 1-15(N52D)-Fab'-PEG was 0.12 μg/ml (in terms of Fab' fragment concentration), whereby it was confirmed that the neutralizing activity of the 1-15(N52D)-Fab' was not influenced even if PEG was added.

In addition, by using the method of Example 6, the 1-15(N52D)-Fab'-PEG was compared to the anti-human NGF antibody tanezumab of the prior art, in terms of the neutralizing activity with respect to human and mouse NGFs. As a result, while IC50 of the 1-15(N52D)-Fab'-PEG was 0.051 μg/ml for the human NGF and 0.069 μg/ml for the mouse NGF, IC50 of the tanezumab was 0.17 μg/ml for the human NGF and 0.23 μg/ml for the mouse NGF. Therefore, it was confirmed that the neutralizing activity of the 1-15(N52D)-Fab'-PEG was about 3.3 times stronger than the tanezumab, with respect to any of the human and mouse NGFs.

Example 14

Analgesic Effect Test Using Mouse Model of Adjuvant-Induced Arthritis

The present inventors evaluated an analgesic effect of the above 1-15(N52D)-Fab'-PEG on a mouse model of adjuvant-induced arthritis.

The 1-15(N52D)-Fab'-PEG was intravenously administered (0.03 mg/kg, 0.1 mg/kg, and 0.3 mg/kg; the dose was 10 mL/kg) to mice, and 1 mg/mL Freund's complete adjuvant (Sigma) was administered in an amount of 25 μL to the hindlimb footpad to induce pain. 24 hours after the pain induction, a rearing behavior for 20 minutes was measured. Specifically, by using SUPERMEX spontaneous activity monitoring system (Muromachi Kikai Co., Ltd.), the number of times of spontaneous rearing behavior of the mice was automatically measured for 20 minutes by using an infrared beam sensor (Matson et al., JPET 320:194-201, 2007). As a comparative control, a prior art antibody tanezumab was used. As a result, while the intravenous administration of the tanezumab produced an analgesic effect of ED50=0.27 mg/kg, the 1-15(N52D)-Fab'-PEG produced an analgesic effect of ED50=0.11 mg/kg which showed an effectiveness greater by about 3 times.

Example 15

Rat Placental Transfer Test

The 1-15(N52D)-Fab'-PEG or the tanezumab was intravenously administered (100 mg/kg, the dose was 10 mL/kg) to female rats in the 17th day of pregnancy. Three days later, antibody concentration in the blood of the mother and fetus was measured.

The antibody concentration was measured in the following manner. The human βNGF (R&D Systems, Inc.) was added to a MULTI-ARRAY Plate (Standard) 96 plate (Meso Scale Discovery) at 25 ng/well and immobilized by being left to stand at room temperature for an hour. The plate was washed three times with the TBST wash solution, and a blocking agent (1% casein TBS; Thermo Fisher) was added thereto and left to stand at room temperature for an hour. Subsequently, a blood sample obtained by diluting blood collected over time was added to the human βNGF-immobilized plate having undergone blocking. After the mixture was reacted at room temperature for 60 minutes under stirring, the plate was washed three times with the TBST wash solution, and then a biotin-labeled anti-human Kappa antibody (Immuno-Biological Laboratories Co., Ltd.) was added thereto. After the mixture was reacted for 60 minutes at room temperature under stirring, the plate was washed three times with the TBST wash solution, and SULFO-TAG-labeled streptavidin (Meso Scale Discovery) was added thereto. After the mixture was reacted for 60 minutes at room temperature under stirring, the plate was washed three times with the TBST wash solution, Read Buffer T (Meso Scale Discovery) was added thereto, and the amount of electrochemical luminescence was measured with SECTOR Imager 6000 (Meso Scale Discovery).

This test was performed on three mother rats. Three days later, the antibody concentration of the 1-15(N52D)-Fab'-PEG and the tanezumab in the blood of the mother rats was 12.1 μg/ml and 7.1 μg/ml on average respectively. Meanwhile, regarding the antibody concentration in the blood of 3 fetuses extracted from each mother rat (9 fetuses in total), while the concentration of 1-15(N52D)-Fab'-PEG in the blood was 0.01 μg/ml (quantitation limit) or less in all fetuses, the concentration of tanezumab in the blood was 5.39 μg/ml on average. That is, while the tanezumab was transferred to the fetus at a rate of 75.9%, the 1-15(N52D)-Fab'-PEG was transferred to the fetus at a rate of 0.08% (detection limit) or less. These results suggested that the 1-15(N52D)-Fab'-PEG is a medical agent which is excellent in safety by avoiding the risk of side effects caused in a fetus due to NGF inhibition.

Example 16

Formation of Immunocomplex (IC)

Whether or not the 1-15(N52D)-Fab'-PEG formed an IC, or how large the size of the formed IC was evaluated. Specifically, 1 mg/ml of the 1-15(N52D)-Fab'-PEG was mixed with the human βNGF (R&D Systems, Inc.) at a molar ratio of 1:1, followed by incubation at room temperature for 3 hours, thereby forming an IC. The particle size and distribution of the IC in this reaction solution were measured using Zetasizer Nano (Malvern) as an instrument measuring dynamic light scattering. For the analysis, a Zetasizer v6.01 (Malvern) was used, and the particle size was indicated by a value (d. nm) analyzed in terms of Intensity (%).

The measured particle sizes are shown in the following Table 1. In this experiment, the particle size of only the NGF was 6.2 nm on average. In the case of only the tanezumab, a peak size was shown at 11.7 nm. When the IC formed by incubating the tanezumab and the NGF was measured, the peak size shifted to 91.3 nm. On the other hand, when an antibody not binding to the NGF was used as a control antibody, the peak size was still 11.7 nm. In consideration of the shifting width, it was assumed that each of the tanezumab and the NGF became a macromolecule as a combination of a plurality of molecules, whereby a large-sized IC was formed. Contrary to this, when IC formation of the 1-15(N52D)-Fab'-PEG and the NGF was measured, the peak size shifted from 18.1 nm to 24.4 nm. In consideration of the shifting width, this result reflected only one-to-one binding and suggested that lattice formation did not occur in the 1-15(N52D)-Fab'-PEG.

TABLE 1

| Sample | | Particle size | |
|---|---|---|---|
| | | Peak (d · nm) | Average (d · nm) |
| Control IgG | IgG | 11.7 | 12.8 |
| | IgG + rhNGF | 11.7 | 12.6 |
| Tanezumab | IgG | 11.7 | 13.0 |
| | IgG + rhNGF | 91.3 | 99.2 |
| 1-15(N52D)-Fab'-PEG | IgG | 18.1 | 19.8 |
| | IgG + rhNGF | 24.4 | 26.0 |

Example 17

Distribution Property into Lesional Tissue

An emulsion including collagen (bovine joint-derived type 2 collagen, 10 mg/mL; Collagen technique workshop) and a complete Freund's adjuvant (0.5 mg/mL; DIFCO) at a ratio of 1:1 was subcutaneously administered to the ankle joint of male DBA/1 mice, thereby preparing collagen-induced arthritis models. Four weeks after the induction of arthritis, the emulsion was administered again to cause arthritis. The degree of development (score and the size of swelling) of the arthritis in hindlimbs was observed to group the mice. Fluorescent labeling was performed on 1 mg/mL PBS solutions of the 1-15(N52D)-Fab'-PEG and the tanezumab by using SAIVI™ Rapid Antibody Labeling Kit, Alexa Fluor (registered trademark) 680 (Life Technologies Corporation). Each solution was administered to the caudal vein at 2 mg/kg (N=4). The fluorescence accumulated in the swollen footpad was analyzed for 50 hours from an hour after the administration by using an IVIS Spectrum (Caliper/Xenogen), and the fluorescence intensity was indicated as numerical values.

FIG. 1 shows temporal change of the amount of antibody retained in the sole. The 1-15(N52D)-Fab'-PEG more clearly showed the retention effect in a lesional tissue compared to the tanezumab, and this effect lasted for 48 hours. From this result, the 1-15(N52D)-Fab'-PEG is considered to efficiently exert an analgesic effect, and it is expected that this antibody will be able to exert an analgesic effect equal to or stronger than the strength of the drug efficacy with a low dose. It is also expected that the 1-15(N52D)-Fab'-PEG can be a medical agent excellent in safety since this antibody is selectively accumulated in a lesional site.

Example 18

Preparation of Amino Acid Adduct of Fab' Fragment

In order to improve the efficiency of PEG introduction into the 1-15(N52D)-Fab', the present inventors prepared Fab' fragments that were obtained by adding two alanines (A) or prolines (P) after the Cys residue in the carboxyl terminal of the heavy-chain fragment and performed expression and purification. The same method as in Example 11 was used to prepare these Fab' fragments. In this method, the codon of the two alanines or prolines were inserted after the codon of the Cys residue of the carboxyl terminal of the heavy-chain fragment of the 1-15(N52D)-Fab', and a stop codon was inserted after this codon.

The base sequence of the heavy-chain fragment of alanine-added 1-15(N52D)-Fab' (a fully human 1-15(N52D-A) antibody Fab' fragment; also referred to as a 1-15(N52D-A)-Fab') is shown by SEQ ID NO:13, and the amino acid sequence thereof is shown by SEQ ID NO:14 respectively. The base sequence of the heavy-chain fragment of proline-added 1-15(N52D)-Fab' (a fully human 1-15(N52D-P) antibody Fab' fragment; also referred to as a 1-15(N52D-P)-Fab') is shown by SEQ ID NO:15, and the amino acid sequence thereof is shown by SEQ ID NO:16 respectively. The light chain of the respective Fab' fragments is the same as the light chain of the 1-15(N52D)-Fab', and the base sequence and the amino acid sequence thereof are shown by SEQ ID NO:11 and SEQ ID NO:12 respectively.

Example 19

Preparation of PEGylated 1-15(N52D-A)-Fab' and Evaluation of Neutralizing Activity and Pharmacological Evaluation 40 kDa PEG was conjugated to the 1-15(N52D-A)-Fab' in the same manner as in Example 13, thereby obtaining PEGylated 1-15(N52D-A)-Fab' (hereinbelow, also referred to as 1-15(N52D-A)-Fab'-PEG).

The neutralizing activity of the 1-15(N52D-A)-Fab'-PEG was evaluated in the method described in Example 3. As a result, while IC50 of the 1-15(N52D)-Fab'-PEG was 0.081±0.034 µg/ml, IC50 of the 1-15(N52D-A)-Fab'-PEG was 0.074±0.021 µg/ml. In addition, IC50 of the tanezumab at this time was 0.410±0.099 µg/ml.

Next, the neutralizing activity was compared using the method described in Example 6. As a result, while IC50 of the 1-15(N52D)-Fab'-PEG was 0.061±0.011 µg/ml for human NGF, IC50 of the 1-15(N52D-A)-Fab'-PEG was 0.064±0.028 µg/ml.

Moreover, the analgesic effect in the adjuvant-induced arthritis model was evaluated using the method described in Example 14. As a result, the 1-15(N52D-A)-Fab'-PEG showed the analgesic effect with respect to the arthritis model.

From the above results, it was confirmed that even if two alanines are added after the Cys residue of the carboxyl terminal, the neutralizing activity and the pharmacological activity are not influenced.

Example 20

Evaluation of Binding Affinity of 1-15(N52D-A)-Fab'-PEG

Thermodynamics in binding of 1-15(N52D-A)-Fab'-PEG and tanezumab to an NGF antigen was examined by Isothermal titration calorimetry (ITC) (Scappaticci F A, J Natl Cancer Inst. 2007, 99:1232-9. Velazquez-Compoy, A., et al, Curr Protoc Cell Biol. 2004, Chapter 17, Unit 17-18). The entire measurement was performed using Auto-iTC 200 manufactured by GE healthcare. During the experiment, a test was performed at the following concentration so as to evaluate binding of a monovalent Fab' fragment to one molecule of antigen, and the entire test was performed in a PBS solution. Specifically, 44 µM of human βNGF (R&D Systems, Inc.) contained in a titration syringe was titrated to calorimeter cells filled with an antibody sample (3 µM of 1-15(N52D-A)-Fab'-PEG or 1.5 µM of tanezumab) at 1.4 µL for 30 times, and the amount of heat produced thereby was detected. The obtained data was analyzed by a Single site binding model by using software attached to the instrument, whereby binding affinity (Kd), a binding ratio (n), binding free energy (ΔG), binding enthalpy (ΔH), and binding entropy (-TΔS) associated with antigen-antibody binding were estimated. The results are shown in Table 2.

As a result, while the value of Kd of tanezumab was 20.41 nM, the value of Kd of 1-15(N52D-A)-Fab'-PEG was 1.49 nM, which showed that the binding affinity of 1-15(N52D-A)-Fab'-PEG was stronger by 10 times or more than that of tanezumab (Table 2).

TABLE 2

|  | Kd (nM) | ΔG (cal/mol) | ΔH (cal/mol) | −TΔS (cal/mol) |
| --- | --- | --- | --- | --- |
| Tanezumab | 20.41 | −10490 | −4759 | −5731 |
| 1-15(N52D-A)-Fab'-PEG | 1.49 | −12041 | −20806 | 8765 |

Example 21

Preparation of PEGylated 1-15(N52D-A)-Fab' Having Various PEG Sizes and Evaluation of Neutralizing Activity The 1-15(N52D-A)-Fab' prepared in Example 18 was conjugated to 5 kDa PEG or 10 kDa PEG by using the similar procedure to that of Example 13. Specifically, Fab' fragment solution prepared by using 20 mM Tris-HCl buffer (pH 7.4) was subjected to reduction treatment by using TCEP. Then, Fab' fragment was collected by using a desalting column. PEG (SUNBRIGHT GL2-SOMA or SUNBRIGHT GL2-100MA; NOF CORPORATION) was added to the obtained Fab' fragment, and the solution was left to stand at 4° C. for a night. The 1-15(N52D-A)-Fab' fragments conjugated to 5 kDa PEG or to 10 kDa PEG which were obtained in this manner are called 1-15(N52D-A)-Fab'-5kPEG and 1-15(N52D-A)-Fab'-10 kPEG, respectively.

Thereafter, by using the method shown in Example 6, the respective PEGylated Fab' fragments were compared with each other in terms of the neutralizing activity. As a comparative control, the 1-15(N52D-A)-Fab'-PEG (conjugated to 40 kDa PEG; hereinbelow, also referred to as 1-15(N52D-A)-Fab'-40 kPEG) prepared in Example 19 was used. At this time, the test was performed at a final NGF concentration of 50 ng/ml. As a result, IC50 of the 1-15(N52D-A)-Fab'-5 kPEG, 1-15(N52D-A)-Fab'-10 kPEG, and 1-15(N52D-A)-Fab'-40 kPEG were 0.030 μg/ml, 0.028 μg/ml, and 0.023 μg/ml, respectively. From these results, it was understood that a PEG size ranging from 5 kDa to 40 kDa did not influence the neutralizing activity of Fab' fragments.

Example 22

Mouse PK Evaluation for PEGylated 1-15(N52D-A)-Fab' Having Various PEG Sizes

Mouse PK evaluation was performed for various types of PEGylated 1-15(N52D-A)-Fab'. Specifically, 0.3 mg/kg of various types of PEGylated 1-15(N52D-A)-Fab' were intravenously administered, and blood was collected 1, 4, 8, 12, 24, 48, 72, 96, and 168 hours after the administration. The amount of tested antibody in the obtained blood was measured by using the sandwich ELISA. Specifically, the tested antibody was added to MSD plate (Meso Scale Discovery) which NGF was immobilized. The antibody bound to the plate was recognized by a biotin-labeled anti-human Kappa antibody, which was then detected by SULFO-TAG-labeled streptavidin. The concentration of the antibody in the blood was calculated by creating a calibration curve by using the respective standards. From the calculated concentration of the antibody in the blood, the antibody half-life in the blood (T1/2: hour) was calculated. As a result, T1/2 of the 1-15(N52D-A)-Fab'-5 kPEG, 1-15(N52D-A)-Fab'-10 kPEG, and 1-15(N52D-A)-Fab'-40 kPEG were 13.8±2.2 hours, 17.7±0.4 hours, and 39.2±3.7 hours, respectively.

Example 23

Analgesic Effect Test Using Rat Plantar Incision Model

By using a rat post-plantar incision pain model (Brennan et al, Current Protocols in Pharmacology 2004; 5.34.1-5.34.8) which is considered to reflect postoperative pain in clinical practice, the analgesic effect of the 1-15(N52D-A)-Fab'-5 kPEG and the 1-15(N52D-A)-Fab'-10 kPEG on postoperative pain was evaluated.

Specifically, 8 rats were assigned to each group, and the 1-15(N52D-A)-Fab'-5 kPEG or -10 kPEG was intravenously administered to the rats (0.1 mg/kg, 0.3 mg/kg, and 1 mg/kg, the dose was 1 mL/kg). Thereafter, in the sole of right hindlimb, a straight incision was made which extended 10 mm toward the toe from a starting point at a position distant by 5 mm from the end of the heel, and then mattress sutures were immediately made with a nylon thread at two sites, thereby inducing pain. Pain thresholds around the operation site were measured after 5 hours and the first, second, third, fourth, and fifth days after the pain induction. For the measurement, a Dynamic plantar anesthesiometer manufactured by Ugo Basile was used to measure a pressure at which the rats showed avoidance behavior when pressure was applied to the sole. As a comparative control, the antibody tanezumab in the prior art was used.

As a result, while intravenous administration of tanezumab resulted in an analgesic effect of ED50=0.26 mg/kg on postoperative day 1, both the 1-15(N52D-A)-Fab'-5 kPEG and -10 kPEG exerted an analgesic effect of ED50=0.15 mg/kg which was about twice as efficacious. In addition, a significant analgesic effect of the 1-15(N52D-A)-Fab'-5 kPEG and -10 kPEG was still observed on postoperative day 3 and 4, respectively.

Example 24

Evaluation of Aggregation Stability

The 1-15(N52D-A)-Fab'-40 kPEG was dissolved at 1 mg/ml and 10 mg/ml under conditions of pH 5, pH 6, pH 7.4, and pH 9. Each of these solutions were placed under a condition of 50° C. so as to evaluate aggregation stability observed after 2 weeks. To evaluate the aggregation property, size exclusion chromatography was performed by using Agilent 1100 manufactured by Agilent. As measurement conditions, 0.1 M sodium phosphate containing 0.2 M arginine (pH 6.8) was used as a buffer of mobile phase, and TSK gel Super Sw3000 (TOSOH, 2.0 mm ID×300 mm) was used as a column. The detection wavelength was 280 nm. In the test at 1 mg/ml, tanezumab was used as comparative antibody, and the results are shown in Table 3. In the test at 10 mg/ml, tanezumab and REGN 475 were used as comparative antibodies, and the results are shown in Table 4.

As a result, for tanezumab and REGN 475, marked increase in the amount of produced aggregates was observed after two weeks. Contrary to this, for the 1-15(N52D-A)-Fab'-40 kPEG, aggregates were almost not detected. This result suggests that the PEGylated 1-15(N52D-A)-Fab' is highly likely to be a drug having excellent storage stability.

TABLE 3

| pH | Time (day) | 1-15(N52D-A)-Fab'-40kPEG Aggregation (%) | | Tanezumab Aggregation (%) | |
|---|---|---|---|---|---|
| | | Polymer | Dimer | Polymer | Dimer |
| pH 5 | 0 | 0.0 | 0.7 | 0.2 | 2.5 |
| | 14 | 0.0 | 0.7 | 11.7 | 5.6 |
| pH 6 | 0 | 0.0 | 0.7 | 0.3 | 2.7 |
| | 14 | 0.0 | 0.6 | 1.3 | 3.8 |
| pH 7.4 | 0 | 0.0 | 0.7 | 0.3 | 2.8 |
| | 14 | 0.0 | 0.6 | 3.1 | 3.8 |
| pH 9 | 0 | 0.0 | 0.6 | 0.3 | 2.8 |
| | 14 | 0.0 | 0.4 | 1.1 | 5.7 | 4.7 |

TABLE 4

| pH | Time (day) | 1-15(N52D-A)-Fab'-40kPEG Aggregation (%) | | Tanezumab Aggregation (%) | | REGN 475 Aggregation (%) | |
|---|---|---|---|---|---|---|---|
| | | Polymer | Dimer | Polymer | Dimer | Polymer | Dimer |
| pH 5 | 0 | 0.0 | 0.4 | 0.9 | 4.8 | 0.3 | 1.7 |
| | 14 | 0.1 | 0.5 | 23.5 | 8.4 | 8.7 | 3.9 |
| pH 6 | 0 | 0.0 | 0.4 | — | — | 1.2 | 3.0 |
| | 14 | 0.0 | 0.7 | — | — | 2.1 | 3.6 |
| pH 7.4 | 0 | 0.0 | 0.5 | 1.7 | 6.1 | 0.3 | 2.0 |
| | 14 | 0.0 | 0.8 | 5.6 | 7.8 | 4.0 | 2.6 |
| pH 9 | 0 | 0.0 | 0.6 | 1.8 | 6.4 | 0.3 | 1.8 |
| | 14 | 0.0 | 1.5 | 7.1 | 7.5 | 12.9 | 2.9 |

— not tested

INDUSTRIAL APPLICABILITY

The anti-human NGF antibody, more specifically, the anti-human NGF antibody Fab' fragment of the present invention is useful for preventing or treating various diseases in which human NGF is involved in the formation of pathological conditions.

---

The invention claimed is:

1. An anti-human NGF antibody Fab' fragment comprising:
   a heavy-chain fragment comprising a heavy-chain variable region consisting of the amino acid sequence of SEQ ID NO:6; and
   a light chain comprising a light-chain variable region consisting of the amino acid sequence of SEQ ID NO:4.

2. The Fab' fragment according to claim 1, wherein the heavy-chain fragment comprises a heavy-chain constant region which is a human Igγ1 constant region.

3. The Fab' fragment according to claim 1, wherein the light chain comprises a light-chain constant region which is a human Igκ constant region 4. The Fab' fragment according to claim 1, wherein the heavy-chain fragment comprises a heavy-chain constant region which is a human Igγ1 constant region, and the light chain comprises a light-chain constant region which is a human Igκ constant region.

5. The Fab' fragment according to claim 1, comprising:
   a heavy-chain fragment consisting of the amino acid sequence of SEQ ID NO:10, SEQ ID NO:14, or SEQ ID NO:16; and
   a light chain consisting of the amino acid sequence of SEQ ID NO:12.

6. The Fab' fragment according to claim 1, wherein the Fab' fragment is conjugated to polyethylene glycol.

7. The Fab' fragment according to claim 2, wherein the Fab' fragment is conjugated to polyethylene glycol.

8. The Fab' fragment according to claim 3, wherein the Fab' fragment is conjugated to polyethylene glycol.

9. The Fab' fragment according to claim 4, wherein the Fab' fragment is conjugated to polyethylene glycol.

10. The Fab' fragment according to claim 5, wherein the Fab' fragment is conjugated to polyethylene glycol.

11. An expression vector comprising a polynucleotide comprising a sequence that encodes a heavy-chain fragment comprising a heavy-chain variable region consisting of the amino acid sequence of SEQ ID NO:6; and a polynucleotide comprising a sequence that encodes a light chain comprising a light-chain variable region consisting of the amino acid sequence of SEQ ID NO:4.

12. An isolated host cell transformed with the expression vector according to Claim 11.

13. An isolated host cell, which is selected from the group consisting of:
   (a) a host cell transformed with an expression vector comprising a polynucleotide comprising a sequence that encodes a heavy-chain fragment comprising a heavy-chain variable region consisting of the amino acid sequence of SEQ ID NO:6 and a polynucleotide comprising sequence that encodes a light chain comprising a light-chain variable region consisting of the amino acid sequence of SEQ ID NO:4; and
   (b) a host cell transformed with an expression vector comprising a polynucleotide comprising a sequence that encodes a heavy-chain fragment comprising a heavy-chain variable region consisting of the amino acid sequence of SEQ ID NO:6and with an expression vector comprising a polynucleotide comprising a sequence that encodes a light chain comprising a light-chain variable region consisting of the amino acid sequence of SEQ ID NO:4.

14. The isolated host cell according to claim 13, wherein said host cell is a host cell transformed with an expression vector comprising a polynucleotide comprising a sequence that encodes a heavy-chain fragment comprising a heavy-chain variable region consisting of the amino acid sequence of SEQ ID NO:6 and with an expression vector comprising a polynucleotide comprising a sequence that encodes a light chain comprising a light-chain variable region consisting of the amino acid sequence of SEQ ID NO:4.

15. A method, comprising:
   expressing an anti-human NGF antibody Fab' fragment by culturing the host cell according to claim 13, thereby producing an anti-human NGF antibody Fab' fragment.

16. A Fab' fragment produced by the method according to claim 15.

17. The Fab' fragment according to claim 16, wherein the Fab' fragment is conjugated to polyethylene glycol.

* * * * *

SEQUENCE LISTING

<160> NUMBER OF SEQ ID NOS: 16

<210> SEQ ID NO 1
<211> LENGTH: 363
<212> TYPE: DNA
<213> ORGANISM: Artificial Sequence
<220> FEATURE:
<223> OTHER INFORMATION: VH gene of anti-human NGF antibody

<400> SEQUENCE: 1

```
caggtgcagc tacagcagtg gggcgcagga ctgttgaagc cttcggagac cctgtccctc      60
acctgcgctg tctatggtgg gtccttcagt ggttactact ggagctgggt ccgccagccc     120
ccagggaagg ggctggagtg gattgggaa atcaatcata gtggaagcac caacaacaac     180
ccgtccctca agagtcgagt caccatatca gtaggcacgt ccaagaacca gttctccctg     240
aagctgagct ctgtgaccgc cgcggacacg gctgtgtatt actgttcgag agatgggggc     300
cccgaatcgg ggatgggggc ttttgatatc tggggccaag gacaatggt caccgtctcc     360 tca                                                                   363
```

<210> SEQ ID NO 2
<211> LENGTH: 121
<212> TYPE: PRT
<213> ORGANISM: Artificial Sequence
<220> FEATURE:
<223> OTHER INFORMATION: VH of anti-human NGF antibody

<400> SEQUENCE: 2

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Ser Trp Val Arg Gln Pro Pro Gly Lys Gly Leu Glu Trp Ile
             35                  40                  45

Gly Glu Ile Asn His Ser Gly Ser Thr Asn Asn Asn Pro Ser Leu Lys
         50                  55                  60
```

```
Ser Arg Val Thr Ile Ser Val Gly Thr Ser Lys Asn Gln Phe Ser Leu
 65                  70                  75                  80

Lys Leu Ser Ser Val Thr Ala Ala Asp Thr Ala Val Tyr Tyr Cys Ser
                 85                  90                  95

Arg Asp Gly Gly Pro Glu Ser Gly Met Gly Ala Phe Asp Ile Trp Gly
            100                 105                 110

Gln Gly Thr Met Val Thr Val Ser Ser
        115                 120

<210> SEQ ID NO 3
<211> LENGTH: 339
<212> TYPE: DNA
<213> ORGANISM: Artificial Sequence
<220> FEATURE:
<223> OTHER INFORMATION: VL gene of anti-human NGF antibody

<400> SEQUENCE: 3
gatattgtga tgactcagtc tccactctcc ctgcccgtca cccctggaga gccggcctcc      60
atctcctgca ggtctagtca gagcctcctg catagtaatg gattcaacta tttgggttgg    120
tacctgcaga agccagggca gtctccacag ctcctgatct atttgggttc taatcgggcc    180
tccggggtcc ctgacaggtt cagtggcagt ggatcaggca cagattttac tctgaaaatc    240
agcagagtgg aggctgagga tgttggggtt tattactgca tgcaagctct acaaactccg    300 tacactttg gccaggggac caagctggag atcaaacgg                            339

<210> SEQ ID NO 4
<211> LENGTH: 113
<212> TYPE: PRT
<213> ORGANISM: Artificial Sequence
<220> FEATURE:
<223> OTHER INFORMATION: VL of anti-human NGF antibody

<400> SEQUENCE: 4

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Gly Phe Asn Tyr Leu Gly Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Tyr Thr Phe Gly Gln Gly Thr Lys Leu Glu Ile Lys
            100                 105                 110

Arg

<210> SEQ ID NO 5
<211> LENGTH: 363
<212> TYPE: DNA
<213> ORGANISM: Artificial Sequence
<220> FEATURE:
<223> OTHER INFORMATION: VH gene of anti-human NGF antibody

<400> SEQUENCE: 5
caggtgcagc tacagcagtg gggcgcagga ctgttgaagc cttcggagac cctgtccctc      60
```

```
acctgcgctg tctatggtgg gtccttcagt ggttactact ggagctgggt ccgccagccc      120 cagggaagg ggctggagtg gattggggaa atcgaccata gtggaagcac caacaacaac      180
ccgtccctca agagtcgagt caccatatca gtaggcacgt ccaagaacca gttctccctg      240
aagctgagct ctgtgaccgc cgcggacacg gctgtgtatt actgttcgag agatgggggc     300
cccgaatcgg ggatgggggc ttttgatatc tggggccaag ggacaatggt caccgtctcc     360
tca                                                                    363
```

```
<210> SEQ ID NO 6
<211> LENGTH: 121
<212> TYPE: PRT
<213> ORGANISM: Artificial Sequence
<220> FEATURE:
<223> OTHER INFORMATION: VH of anti-human NGF antibody

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser
        115                 120
```

```
<210> SEQ ID NO 7
<211> LENGTH: 693
<212> TYPE: DNA
<213> ORGANISM: Artificial Sequence
<220> FEATURE:
<223> OTHER INFORMATION: H-chain fragment gene of anti-human NGF
      antibody

<400> SEQUENCE: 7
caggtgcagc tacagcagtg gggcgcagga ctgttgaagc cttcggagac cctgtccctc       60
acctgcgctg tctatggtgg gtccttcagt ggttactact ggagctgggt ccgccagccc      120 cagggaagg ggctggagtg gattggggaa atcaatcata gtggaagcac caacaacaac      180
ccgtccctca agagtcgagt caccatatca gtaggcacgt ccaagaacca gttctccctg      240
aagctgagct ctgtgaccgc cgcggacacg gctgtgtatt actgttcgag agatgggggc     300
cccgaatcgg ggatgggggc ttttgatatc tggggccaag ggacaatggt caccgtctcc     360
tcagcctcca ccaagggccc atcggtcttc cccctggcac cctcctccaa gagcacctct     420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actccttag tagcgtggtg accgtgccct ccagcagctt gggcacccag     600
acctacatct gcaacgtgaa tcacaagccc agcaacacca aggtggacaa gaaagttgag     660
```
cccaaatctt gtgacaaaac tcacacatgc tga        693

<210> SEQ ID NO 8
<211> LENGTH: 230
<212> TYPE: PRT
<213> ORGANISM: Artificial Sequence
<220> FEATURE:
<223> OTHER INFORMATION: H-chain fragment of anti-human NGF antibody

<400> SEQUENCE: 8

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asn His Ser Gly Ser Thr Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys
225                 230
```

<210> SEQ ID NO 9
<211> LENGTH: 693
<212> TYPE: DNA
<213> ORGANISM: Artificial Sequence
<220> FEATURE:
<223> OTHER INFORMATION: H-chain fragment gene of anti-human NGF
      antibody

<400> SEQUENCE: 9
caggtgcagc tacagcagtg gggcgcagga ctgttgaagc cttcggagac cctgtccctc        60
acctgcgctg tctatggtgg gtccttcagt ggttactact ggagctgggt ccgccagccc       120
ccagggaagg gctggagtg gattgggaa atcgaccata gtggaagcac caacaacaac        180
ccgtccctca agagtcgagt caccatatca gtaggcacgt ccaagaacca gttctccctg       240
aagctgagct ctgtgaccgc cgcggacacg gctgtgtatt actgttcgag agatgggggc       300

```
cccgaatcgg ggatgggggc ttttgatatc tggggccaag ggacaatggt caccgtctcc    360
tcagcctcca ccaagggccc atcggtcttc ccctggcac cctcctccaa gagcacctct     420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actcccttag tagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc tga                                 693
```

\<210\> SEQ ID NO 10
\<211\> LENGTH: 230
\<212\> TYPE: PRT
\<213\> ORGANISM: Artificial Sequence
\<220\> FEATURE:
\<223\> OTHER INFORMATION: H-chain fragment of anti-human NGF antibody

\<400\> SEQUENCE: 10

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys
225                 230
```

\<210\> SEQ ID NO 11
\<211\> LENGTH: 660
\<212\> TYPE: DNA
\<213\> ORGANISM: Artificial Sequence
\<220\> FEATURE:
\<223\> OTHER INFORMATION: L-chain gene of anti-human NGF antibody

\<400\> SEQUENCE: 11

```
gatattgtga tgactcagtc tccactctcc ctgcccgtca cccctggaga gccggcctcc    60
atctcctgca ggtctagtca gagcctcctg catagtaatg gattcaacta tttgggttgg   120
tacctgcaga agccagggca gtctccacag ctcctgatct atttgggttc taatcgggcc   180
tccggggtcc ctgacaggtt cagtggcagt ggatcaggca cagattttac tctgaaaatc   240
agcagagtgg aggctgagga tgttggggtt tattactgca tgcaagctct acaaactccg   300 tacactttg gccaggggac caagctggag atcaaacgga ctgtggctgc accatctgtc    360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

<210> SEQ ID NO 12
<211> LENGTH: 219
<212> TYPE: PRT
<213> ORGANISM: Artificial Sequence
<220> FEATURE:
<223> OTHER INFORMATION: L-chain of anti-human NGF antibody

<400> SEQUENCE: 12

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Phe Asn Tyr Leu Gly Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 13
<211> LENGTH: 699
<212> TYPE: DNA
<213> ORGANISM: Artificial Sequence
<220> FEATURE:
<223> OTHER INFORMATION: H-chain fragment gene of anti-human NGF antibody

<400> SEQUENCE: 13

```
caggtgcagc tacagcagtg gggcgcagga ctgttgaagc cttcggagac cctgtccctc    60
acctgcgctg tctatggtgg gtccttcagt ggttactact ggagctgggt ccgccagccc   120
ccagggaagg gctggagtg gattggggaa atcgaccata gtggaagcac caacaacaac   180
ccgtccctca agagtcgagt caccatatca gtaggcacgt ccaagaacca gttctccctg   240
aagctgagct ctgtgaccgc cgcggacacg gctgtgtatt actgttcgag agatgggggc   300
cccgaatcgg ggatggggc ttttgatatc tggggccaag gacaatggt caccgtctcc   360
tcagcctcca ccaagggccc atcggtcttc cccctggcac cctcctccaa gagcacctct   420
gggggcacag cggccctggg ctgcctggtc aaggactact ccccgaacc ggtgacggtg   480
tcgtggaact caggcgccct gaccagcggc gtgcacacct tcccggctgt cctacagtcc   540
tcaggactct actcccttag tagcgtggtg accgtgccct ccagcagctt gggcacccag   600
acctacatct gcaacgtgaa tcacaagccc agcaacacca aggtggacaa gaaagttgag   660
cccaaatctt gtgacaaaac tcacacatgc gcagcctga                         699
```

<210> SEQ ID NO 14
<211> LENGTH: 232
<212> TYPE: PRT
<213> ORGANISM: Artificial Sequence
<220> FEATURE:
<223> OTHER INFORMATION: H-chain fragment of anti-human NGF antibody

<400> SEQUENCE: 14

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Val Arg Gln Pro Pro Gly Lys Gly Leu Glu Trp Ile
         35                  40                  45

Gly Glu Ile Asp His Ser Gly Ser Thr Asn Asn Asn Pro Ser Leu Lys
     50                  55                  60

Ser Arg Val Thr Ile Ser Val Gly Thr Ser Lys Asn Gln Phe Ser Leu
 65                  70                  75                  80

Lys Leu Ser Ser Val Thr Ala Ala Asp Thr Ala Val Tyr Tyr Cys Ser
                 85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

Lys Pro Ser Asn Thr Lys Val Asp Lys Lys Val Glu Pro Lys Ser Cys
    210                 215                 220

Asp Lys Thr His Thr Cys Ala Ala
225                 230

<210> SEQ ID NO 15
<211> LENGTH: 699
<212> TYPE: DNA
<213> ORGANISM: Artificial Sequence
<220> FEATURE:
<223> OTHER INFORMATION: H-chain fragment gene of anti-human NGF
      antibody

<400> SEQUENCE: 15
caggtgcagc tacagcagtg gggcgcagga ctgttgaagc cttcggagac cctgtccctc      60
acctgcgctg tctatggtgg gtccttcagt ggttactact ggagctgggt ccgccagccc     120
ccagggaagg gctggagtg gattggggaa atcgaccata gtggaagcac caacaacaac      180
ccgtccctca gagtcgagt caccatatca gtaggcacgt ccaagaacca gttctccctg      240
aagctgagct ctgtgaccgc cgcggacacg gctgtgtatt actgttcgag agatgggggc     300
cccgaatcgg ggatggggc ttttgatatc tggggccaag ggacaatggt caccgtctcc      360
tcagcctcca ccaagggccc atcggtcttc cccctggcac cctcctccaa gagcacctct     420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actcccttag tagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtga                           699

<210> SEQ ID NO 16
<211> LENGTH: 232
<212> TYPE: PRT
<213> ORGANISM: Artificial Sequence
<220> FEATURE:
<223> OTHER INFORMATION: H-chain fragment of anti-human NGF antibody

<400> SEQUENCE: 16

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Val Arg Gln Pro Pro Gly Lys Gly Leu Glu Trp Ile
        35                  40                  45

Gly Glu Ile Asp His Ser Gly Ser Thr Asn Asn Asn Pro Ser Leu Lys
    50                  55                  60

Ser Arg Val Thr Ile Ser Val Gly Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Arg Asp Gly Gly Pro Glu Ser Gly Met Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val

-continued

```
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro
225                 230
```